(12) United States Patent
White (10) Patent No.: US 11,985,951 B2
(45) Date of Patent: *May 21, 2024

(54) CITRUS GREENING RESISTANT ORANGE TREES AND RELATED METHODS THEREOF

(71) Applicant: Randy Wayne White, Sanibel, FL (US)

(72) Inventor: Randy Wayne White, Sanibel, FL (US)

(73) Assignee: Randy Wayne White, Sanibel, FL (US)

( * ) Notice: Subject to any disclaimer, the term of this patent is extended or adjusted under 35 U.S.C. 154(b) by 0 days.

This patent is subject to a terminal disclaimer.

(21) Appl. No.: 17/510,124

(22) Filed: Oct. 25, 2021

(65) Prior Publication Data

US 2022/0287263 A1 Sep. 15, 2022

Related U.S. Application Data

(63) Continuation of application No. 16/478,808, filed as application No. PCT/US2018/014084 on Jan. 17, 2018, now Pat. No. 11,185,031.

(60) Provisional application No. 62/447,795, filed on Jan. 18, 2017.

(51) Int. Cl.
| | | |
|---|---|---|
| *A01H 5/10* | (2018.01) | |
| *A01G 2/30* | (2018.01) | |
| *A01G 17/02* | (2006.01) | |
| *A01H 6/78* | (2018.01) | |

(52) U.S. Cl.
CPC .............. *A01H 6/785* (2018.05); *A01G 2/30* (2018.02); *A01G 17/02* (2013.01); *A01H 5/10* (2013.01)

(58) Field of Classification Search
None
See application file for complete search history.

(56) References Cited

U.S. PATENT DOCUMENTS

| | | | |
|---|---|---|---|
| 11,185,031 B2 * | 11/2021 | White | A01H 5/10 |
| 2008/0271211 A1 | 10/2008 | Polston et al. | |
| 2015/0047083 P1 | 2/2015 | Grosser | |
| 2015/0067918 A1 | 3/2015 | Kress | |
| 2015/0195973 P1 | 7/2015 | Grosser | |
| 2015/0237782 P1 * | 8/2015 | Grosser | A01H 6/78 Plt./201 |
| 2015/0237783 P1 | 8/2015 | Grosser | |

FOREIGN PATENT DOCUMENTS

| | | |
|---|---|---|
| WO | WO-2013112997 A1 | 8/2013 |
| WO | WO-2015187944 A2 | 12/2015 |
| WO | WO-2018136540 A1 | 7/2018 |

OTHER PUBLICATIONS

Albrecht et al., Influence of rootstock variety on Huanglongbing disease development in field-grown sweet orange (*Citrus sinenis* [L.] Osbeck) trees. Scientia Horticulturae 138: 210-220(2012).
Santa Ana, Spinach genes may stop deadly citrus disease. AgriLife Today. Mar. 26, 2012, pp. 1-5 [Retrieved from the internet: Feb. 28, 2018: https://today.agrilife.org/2012/03/26/transgenic-citrus-trees/ ].
Gong et al., Genetic transformation and genes for resistance to abiotic and biotic stresses in Citrus and its related genera. Plant Cell Tiss. Organ Cult. 113:137-147 (2013).
Hussain et al., Physiological analysis of salt stress behaviour of citrus species and genera: Low chloride accumulation as an indicator of salt tolerance. South African Journal of Botany 81:103-112 (2012).
Levy et al., Ranking the salt tolerance of citrus rootstocks by juice analysis. Scientia Horticulturae. 45(1-2):89-98 (1990).
Levy et al., The response of several citrus genotypes to high-salinity irrigation water. HortScience. 34(5):878-881 (1999).
PCT/US2018/014084 International Search Report and Written Opinion dated May 15, 2018.
PCT/US2018/014084 Invitation to Pay Additional Fees dated Mar. 8, 2018.
Ream et al., Salt tolerance of some Citrus species, relatives, and hybrids tested as rootstocks. J. Amer Soc Hort Sci. 101(3):265-267(1976).
Stover et al., Conventional Citrus of Some Scion/Rootstock Combinations Show Field Tolerance under High Huanglongbing Disease Pressure. HortScience 51(2):127-132 (2016).
U.S. Appl. No. 16/478,808 Final Office Action dated Apr. 9, 2021.
U.S. Appl. No. 16/478,808 Non-Final Office Action dated Sep. 16, 2020.
U.S. Appl. No. 16/478,808 Notice of Allowance dated Aug. 4, 2021.

* cited by examiner

*Primary Examiner* — Medina A Ibrahim
(74) *Attorney, Agent, or Firm* — W.S. G. & R.

(57) ABSTRACT

A composite orange tree having a fruiting cultivar scion grafted to a citrus-greening resistant, or a salinity-resistant rootstock, or a rootstock having both citrus-greening and salinity resistance, is described herein, as are methods of growing such a composite orange tree.

18 Claims, 1 Drawing Sheet

CITRUS GREENING RESISTANT ORANGE TREES AND RELATED METHODS THEREOF

CROSS-REFERENCE

This application is a continuation of U.S. patent application Ser. No. 16/478,808, filed Jul. 17, 2019, which is a national stage entry of International Application No. PCT/US18/14084, filed Jan. 17, 2018, which claims the benefit of U.S. Provisional Application No. 62/447,795, filed Jan. 18, 2017, which application is incorporated herein by reference in its entirety.

BACKGROUND

Citrus greening disease, also known as Huanglongbing (HLB), can significantly impair the productivity of a wide range of orange tree cultivars. The disease has been found on multiple continents, and has significantly impacted citrus production in North America, Africa, South and East Asia, the Arabian Peninsula and elsewhere.

There is no cure for citrus greening disease. Efforts to control the disease typically involve pesticide use, for example pesticides targeting the pathogen and/or the vector responsible for its transmission, but may be hampered by difficulty in maintaining, regenerating and/or studying of diseased plants.

SUMMARY

Described herein are composite citrus trees, such as composite orange trees, which demonstrate desired resistance to citrus greening disease and/or desired resistance to water having elevated salt content, and methods of producing such citrus trees.

According to some aspects, a composite orange tree may comprise a fruiting cultivar scion grafted to a citrus-greening resistant rootstock.

In some embodiments, the composite orange tree comprises a plurality of ripe orange fruits. Often, at least some of the plurality of ripe orange fruits have a sweet taste when ripe. In some embodiments, at least some of the plurality of ripe orange fruits have an orange color on at least part, up to their entire undersurface.

The citrus-greening resistant rootstock is derived from a feral citrus-greening resistant orange tree, or alternately is derived from a cultivated citrus-greening resistant orange tree. The citrus-greening resistant rootstock is alternately derived from a non-transgenic citrus-greening resistant orange tree or from a transgenic citrus-greening resistant orange tree. Some citrus-greening resistant rootstock is derived from a seed obtained from a feral or wild cultivar or is derived from a plant sharing an allele present in a seed obtained from a feral or wild cultivar and the allele is absent from the fruiting cultivar. Often, the citrus-greening resistant rootstock is a rootstock derived from a plant sharing an allele present in a seed obtained from a feral or wild cultivar, the allele is absent from the fruiting cultivar, and the rootstock is transgenic.

In some cases, the composite orange tree is not contacted to pesticide under a dosage regimen sufficient to prevent citrus greening, and nonetheless does not exhibit citrus greening. Often, the composite orange tree is contacted to a citrus greening disease bacterium, or to a citrus greening disease vector, or to both a citrus greening disease bacterium and to a citrus greening disease vector.

Disclosed herein are methods of generating a citrus-greening resistant orange tree can include mutagenizing at least one citrus plant cell having a resistant allele, such as an allele present in genetic material obtained from a feral or wild cultivar and absent from a citrus-greening sensitive citrus plant. Some methods comprise contacting the citrus plant having said allele to at least one citrus-greening bacterium.

Some methods comprise grafting a rootstock comprising said at least one citrus plant cell to a high yield citrus scion.

Some methods of growing a citrus fruit in a citrus-greening environment comprise grafting a fruiting cultivar scion to a citrus-greening resistant rootstock.

Often, the citrus fruit has a sweet taste when ripe. Alternately or in combination, the citrus fruit has an orange color on its lower surface.

In some aspects, the citrus-greening resistant rootstock is derived from a feral citrus-greening resistant orange tree or from a cultivated citrus-greening resistant orange tree. In some cases, the citrus-greening resistant rootstock is derived from a non-transgenic citrus-greening resistant orange tree, or alternately, citrus-greening resistant rootstock is derived from a transgenic citrus-greening resistant orange tree. In some cases, the citrus-greening resistant rootstock is a rootstock derived from a seed obtained from a feral or wild cultivar. Often, the citrus-greening resistant rootstock is a rootstock derived from a plant sharing an allele present in a resistant citrus line, such as a line represented in a seed obtained from a feral or wild cultivar and the allele is absent from the fruiting cultivar. In some embodiments, the citrus-greening resistant rootstock is a rootstock derived from a plant sharing an allele present in a seed obtained from a feral or wild cultivar, where the allele is absent from the fruiting cultivar, and wherein the rootstock is transgenic.

The composite orange tree exhibits at least some resistance to citrus greening. Accordingly, often the composite orange tree is not contacted to pesticide under a dosage regimen sufficient to prevent citrus greening. In some embodiments, the composite orange tree is contacted to a citrus greening disease bacterium, or to a citrus greening disease vector, or to both a citrus greening disease bacterium and citrus greening disease vector.

Some citrus-greening resistant transgenic plants include a cell of a citrus-greening sensitive citrus plant into which a mutation is introduced, said mutation mimicking an allele present in genetic material obtained from a feral or wild cultivar and absent in a non-transgenic citrus-greening sensitive citrus plant.

Said allele is often present in genomic sequence of genetic material obtained from a feral or wild cultivar and is absent from commercially grown orange lines. The allele arises in various cases from a point mutation, often but not necessarily always introduced through TILLING. In some embodiments, said mutation is introduced through sequence—specific mutagenesis, such as through CRISPR. In some embodiments, said mutation comprises a transgene. In some embodiments, said mutation comprises a copy of a coding region of said allele present in genetic material obtained from a feral or wild cultivar and absent in a non-transgenic citrus-greening sensitive citrus plant.

According to some aspects, a citrus plant includes at least one first allele present in commercially grown orange lines and absent from a feral or wild cultivar and at least one second allele absent in commercially grown orange lines and present in a feral or wild cultivar.

Some resistant citrus plants are progeny of a high-yield plant crossed to citrus greening resistant plant. In some embodiments, said citrus plant resembles commercially grown orange lines at least 75% of loci where the commercially grown orange line differs from a feral or wild cultivar.

In some embodiments, said citrus plant resembles commercially grown orange lines at least 87% of loci where commercially grown orange lines differs from a feral or wild cultivar. In some embodiments, said citrus plant resembles commercially grown orange lines at least 87% of loci where commercially grown orange lines differs from a feral or wild cultivar. In some embodiments, said citrus plant resembles commercially grown orange lines at least 93% of loci where commercially grown orange lines differs from a feral or wild cultivar.

In some embodiments, said citrus plant is transgenic. In some embodiments, said citrus plant is a hybrid. In some embodiments, said citrus plant descends from a feral or wild cultivar.

A citrus plant is provided herein that yields commercially viable fruit following exposure to citrus greening disease, even where the plant is exposed to a pesticide level insufficient to protect a citrus-greening sensitive plant.

The plant is often a graft or a hybrid.

Root tissue of the citrus plant often comprises an allele absent from the citrus-greening sensitive plant. Root tissue of the citrus plant often comprises an allele present in a feral or wild cultivar and absent from the citrus-greening sensitive plant. Often, root tissue of the citrus plant comprises an allele present in a feral or wild cultivar and the root tissue is derived from a feral or wild cultivar.

Some plants disclosed herein yield commercially viable fruit when exposed to a level of pesticide insufficient to prevent citrus greening in nonresistant plants, in some cases even when the pesticide level is zero.

In some embodiments, the plant yields commercially viable fruit at least 1 year after exposure to the citrus-greening disease.

According to some aspects, a citrus plant is provided that requires no more than about 95%, 90%, 80%, 70%, 60%, 50%, 40%, 30%, 20%, 10%, 5%, or less than 5% of standard pesticide amount to yield commercially viable fruit following exposure to citrus greening disease.

Often but not always, the plant is a graft. In some cases, the plant is a hybrid.

Root tissue of the citrus plant, in some aspects, comprises an allele absent from a citrus-plant sensitive to the citrus greening disease. In some embodiments, root tissue of the citrus plant comprises an allele present in a feral or wild cultivar and absent from a citrus plant sensitive to the citrus greening disease. In some embodiments, root tissue of the citrus plant comprises an allele present in a feral or wild cultivar and the root tissue is derived from a feral or wild cultivar.

Plants disclosed herein often yield commercially viable fruit at least 1 year after exposure to the citrus-greening disease. Citrus plants provided herein often demonstrate improved viability following exposure to citrus greening disease compared to a plant sensitive to citrus greening disease. Such plants are often at least one of grafts, hybrids and transgenic.

Often, root tissue of the citrus plant comprises an allele absent from the citrus plant sensitive to citrus greening disease. In some embodiments, root tissue of the citrus plant comprises an allele present in a feral or wild cultivar and absent from the citrus plant sensitive to citrus greening disease. In some embodiments, root tissue of the citrus plant comprises an allele present in a feral or wild cultivar and the root tissue of the citrus plant is derived from a feral or wild cultivar.

Often, the citrus plant demonstrates improved viability at least 1 year after exposure to the citrus-greening disease.

Some citrus plants disclosed herein exhibit reduced symptoms of citrus greening disease following exposure to citrus greening disease compared to a citrus plant sensitive to citrus greening disease. Such plants are often at least one of grafts, hybrids and transgenic.

Often, root tissue of the citrus plant that exhibits reduced symptoms comprises an allele absent from the citrus plant sensitive to the citrus greening disease. For example, root tissue the citrus plant that exhibits reduced symptoms comprises an allele present in a feral or wild cultivar and absent from the citrus plant sensitive to the citrus greening disease. Root tissue of the citrus plant that exhibits reduced symptoms may comprise an allele present in a feral or wild cultivar and the root tissue is derived from a feral or wild cultivar. Citrus plants disclosed herein often exhibit reduced symptoms at least 1 year after exposure to the citrus-greening disease.

A method of growing a plant is provided which uses reduced pesticide can include grafting a fruiting cultivar to a citrus-greening resistant rootstock and administering no more than about 95%, 90%, 80%, 70%, 60%, 50%, 40%, 30%, 20%, 10%, 5%, or less than 5% of standard pesticide amount to yield commercially viable fruit following exposure to citrus greening disease of a standard pesticide amount.

According to some aspects, provided herein is a citrus plant that yields commercially viable fruit after exposure to water having elevated salt content. The exposure is variously an acute exposure, such as that which results from a storm surge of sea water into a costal growth area, or chronic exposure, as results from sea water encroaching into the water table of a citrus growth area. Alternately or in combination, the exposure is in some cases resultant from chronic or acute watering of a citrus plant or plants using water having a salinity content sufficient to impair or prohibit production of commercially viable fruit yield.

In some cases, the plant is a graft. Often, the rootstock of the graft may be resistant to the water having the elevated salt content. In some cases the rootstock is able to selectively exclude salt ions from water uptake, or to selectively sequester or otherwise retain salt ions in the roots, or to otherwise supply the scion of the graft with water of a salinity sufficient to allow growth up to and including production of a commercially viable fruit yield.

In some cases, the plant is a hybrid. In some cases, the plant is transgenic. In some cases the roots are able to selectively exclude salt ions from water uptake, or to selectively sequester or otherwise retain salt ions in the roots, or to otherwise supply the above-ground part of the plant of with water of a salinity sufficient to allow growth up to and including production of a commercially viable fruit yield.

The plant may be resistant to citrus-greening. In some cases, the plant yields commercially viable fruit at least 1 year after exposure to the citrus-greening disease.

In some cases, the plant is grown using a watering regimen which provides a quantity of fresh water to the plant that is no more than 80% that provided to a corresponding commercial citrus plant, including no more than 50%. In some cases, no or substantially no fresh water is provided to the plant in a watering regimen.

In some cases, the plant maintains commercial viability after 1 year of growth in the water with elevated salt content, including after 5 years.

The plant may be grown at sea level. In some cases, the salt content of the water with elevated salt content is about 1,000 ppm to about 35,000 ppm, including about 5,000 ppm to about 30,000 ppm.

According to some aspects, a citrus tree provided herein has at least one allele common to a feral or wild cultivar, such as a feral or wild cultivar for which seeds or genetic information is deposited in a repository available for public inspection and absent from at least one commercial citrus tree line.

In some cases, the tree has at least about 50% of alleles in common with the at least one commercial citrus tree line, including at least about 75%, at least about 87% or at least about 93%.

According to some aspects, provided herein is a graft tree having a root stock that is resistant to water having elevated levels of salt content.

The salt content may be about 1,000 ppm to about 35,000 ppm.

In some cases, the tree is resistant to citrus-greening. Often the tree yields commercially viable fruit at least 1 year after exposure to the citrus-greening disease.

Often the tree yields commercially viable fruit at least 1 year after exposure to the water having the elevated levels of salt.

In some cases, the tree yields commercially viable fruit after exposure to a watering regimen comprising providing a quantity of fresh water to the plant that is no more than about 80% that provided to a corresponding commercial citrus plant, including no more than about 50%. In some cases, no or substantially no fresh water is provided to the tree in a watering regimen.

In some cases, the tree has at least about 50% of alleles in common with at least one commercial citrus tree line, including at least about 75%, at least about 87%, or at least about 93%.

INCORPORATION BY REFERENCE

All publications, patents, and patent applications mentioned in this specification are herein incorporated by reference to the same extent as if each individual publication, patent, or patent application was specifically and individually indicated to be incorporated by reference.

BRIEF DESCRIPTION OF THE DRAWINGS

A better understanding of the features and advantages of the present invention will be obtained by reference to the following detailed description that sets forth illustrative embodiments, in which the principles of the invention are utilized, and the accompanying drawings of which.

DETAILED DESCRIPTION

The present disclosure relates to composite citrus trees, including composite orange trees, and methods of producing such composite citrus trees, having increased resistance to citrus greening. For example, the composite orange trees may include a fruiting cultivar scion grafted onto a citrus greening disease resistant rootstock, where sweet oranges of the fruiting cultivar can be produced by the composite orange trees even with exposure of the tree to the pathogen which causes citrus greening disease. The composite citrus tree may demonstrate increased resistance to water having elevated salt content, such as brackish water.

Grafting is a technique which comprises joining of tissues from two or more different plants to form one composite plant. For example, grafting can include joining of plant segments from two different plants to form a graft union at the site where the two plant segments are joined. A vascular connection between the two plant segments is formed at the site of the graft union such that transport of water and/or nutrients occurs between the joined plant segments to enable growth of the composite plant. An upper part of a first plant, for example a scion, can be grafted onto a lower part of a second plant, for example a rootstock, to form the composite plant. Once grafting is complete, water and/or nutrients can be transported between the rootstock and the scion, such as to support growth of the scion.

A number of commercially grown citrus lines are known. Most commercial citrus lines are known to lack resistance to citrus greening. The citrus greening disease may affect a number of commercial orange cultivars, including the Washington Navel, Valencia, Trovita, Hamlin, Shamouti, Parson Brown, Pineapple, Queen, Sunstar, Gardner, and Mid-Sweet, Blood Oranges, Lue Gim Gong, Rhode Island Valencia and/or the Homosassa. As described in further details herein, a scion of one or more of these commercial orange cultivars can be grafted onto a citrus greening resistant rootstock to provide a composite orange tree which demonstrates desired resistance to the citrus greening disease. In some embodiments, fruiting cultivar scions of other types of commercial citrus plants can be grafted to a citrus greening resistant rootstock to provide a composite citrus tree demonstrating desired resistance to citrus greening disease. In some embodiments, other types of commercial citrus plants include commercial fruiting cultivars of limes, lemons, pomelos, tangerines, and/or grapefruits.

Some resistant plants disclosed herein comprise a composite citrus tree, such as a composite orange tree, including as its fruiting cultivar scion any of a number of the commercially available cultivars known to be susceptible to the citrus greening disease. The resulting composite orange trees may demonstrate desired resistance to the citrus greening disease such that fruits borne by the trees ripen into sweet oranges, often demonstrating a yield comparable to that of the commercially available cultivar in the absence of citrus greening. The composite orange trees may demonstrate maintained productivity of sweet oranges after exposure to pathogens which cause the citrus greening disease, without or substantially without use of pesticides that treat and/or mitigate the disease, or without using a sufficient quantity of pesticides which are designed to remedy the disease.

Citrus greening disease, also known as Huanglongbing (HLB), is a disease which impairs one or more of fruit ripening, fruit sweetening, and fruit color change. The disease is vector transmitted. The bacterium *Candidatus* Liberibacter *asiaticus*, for example transmitted by psyllids, including Asian citrus psyllids and African citrus psyllids, is a likely cause of the disease.

Citrus greening damages all parts of an orange tree. The disease may affect one or more of the leaf, twig, root system and fruit of the orange tree. Adverse effects of orange trees infected with the disease can progress from one branch of the tree to the entire tree. Infection often eventually affects plant viability, with infected plants typically surviving no more than about 3 to about 5 years. In some cases, infection of the orange tree with citrus greening eventually results in death of the tree.

Roots are often the earliest affected organs, such that by the time that above-ground organs exhibit symptoms, the disease has already progressed in the roots such that the plant is unlikely to survive for more than 3-5 years. While in the roots, the pathogen that causes citrus greening disease can replicate and damage the roots. Damaged roots can starve the trees, for example preventing or limiting absorption of nutrients from the soil. The pathogen can spread to other parts of the tree, spreading the damage to the other parts of the tree. In some instances, damage to roots of trees results in significant loss of the fibrous roots of the trees. Root systems of infected trees may be poorly developed. The disease may suppress new root growth. A tree may experience a loss of about 30% to about 50% of the fibrous root before symptoms are observed above-ground. In some cases, the bacterium colonizes the roots before spreading to the fruiting parts and/or leaf parts. Often symptoms in fruiting and/or leaf parts are manifested after root damage has already occurred. Although symptoms in fruiting parts may have the most direct economic impact, by the time symptoms are observed in leaf parts and/or fruiting parts of the tree, many trees have already suffered irreparable root damage. Restoration of the health of trees which have experienced irreparable root damage will often be difficult or unsuccessful, with the trees eventually dying. As such, direct fruit and/or leaf treatment may be insufficient to restore productivity of trees showing symptoms in its leaf parts and/or fruiting parts. Thus, a remedy that protects orange tree roots from damage shows greatest promise as a protection against HLB.

Symptoms seen in the leaves of orange trees afflicted by the citrus greening disease can include one or more of yellowing of veins of the leaves and asymmetrical chlorosis. Varying degrees of asymmetrical chlorosis, which may also be referred to as "blotchy mottle," can be seen on leaves of varieties of sweet oranges afflicted with the citrus greening disease. In some cases, some leaves may lack any green color or may have some patches of green color. In some cases, the leaves may be small and upright. For example, the leaves may be small and upright, and show varying degrees of asymmetric chlorosis. Chlorotic patterns of leaves afflicted by the disease may be similar to that of leaves of citrus trees with one or more types of mineral deficiencies (e.g., zinc, iron, and/or manganese). In some cases, the asymmetric chlorosis of leaves infected with the citrus greening disease may resemble that observed with other ailments, including infection by citrus tristeza virus (CTV), phytophthora root rot, water logging, citrus blight, leafminer tunnels or and/or citrus stubborn disease. The yellowing of the veins and/or development of asymmetric chlorosis may start with one shoot or branch and spread to other shoots of the tree Branches of orange trees infected by the citrus greening disease may show yellowing shoots, stunted growth and/or twig dieback. The orange trees may have off-season blooms which fall off without producing fruits and/or producing irregular fruits, as described in further details herein.

Adverse effects on the health of orange trees can be observed in the fruits. The diseased trees can bear fewer and/or smaller fruits, for example exhibiting declined productivity. The decline in productivity may be observed within a few years of initial infection. Fruits borne by infected trees may prematurely drop. The fruits may be bitter in taste rather than sweet, including having a salty and bitter taste. The fruits may be irregularly shaped. The fruits may be lopsided. In some cases, the fruits may have a curved central core. In some cases, the orange fruits may fail to color properly, for example retaining a green color on at least a portion of the fruit. In some cases, the entire fruit may retain a green color and fail to color properly. In some cases, the portion of the fruits at the stylar end may not color properly, retaining a green colored stylar end. In some cases, a yellow stain may be present beneath the peduncle (stem) of the fruit, for example beneath the calyx button. Such a yellow stain may be observable when the fruit is cut. The affected fruit may also contain aborted seeds.

Grafting can be used to create a composite citrus tree in which a cultivar scion and a citrus-greening resistant rootstock are joined. Often at least one scion is grafted to at least one rootstock. Sometimes more than one scion is grafted to a single rootstock. Generally an end of a scion is brought together with an end of a rootstock to form a graft union. Tissue can form around a graft union and can serve as a conduit for water and nutrients between the rootstock and the scion. Exemplary methods of grafting include, but are not limited to, stem grafting, bud grafting, bark grafting, cleft barking, splice grafting, side grafting, and saddle grafting.

Figure 1:
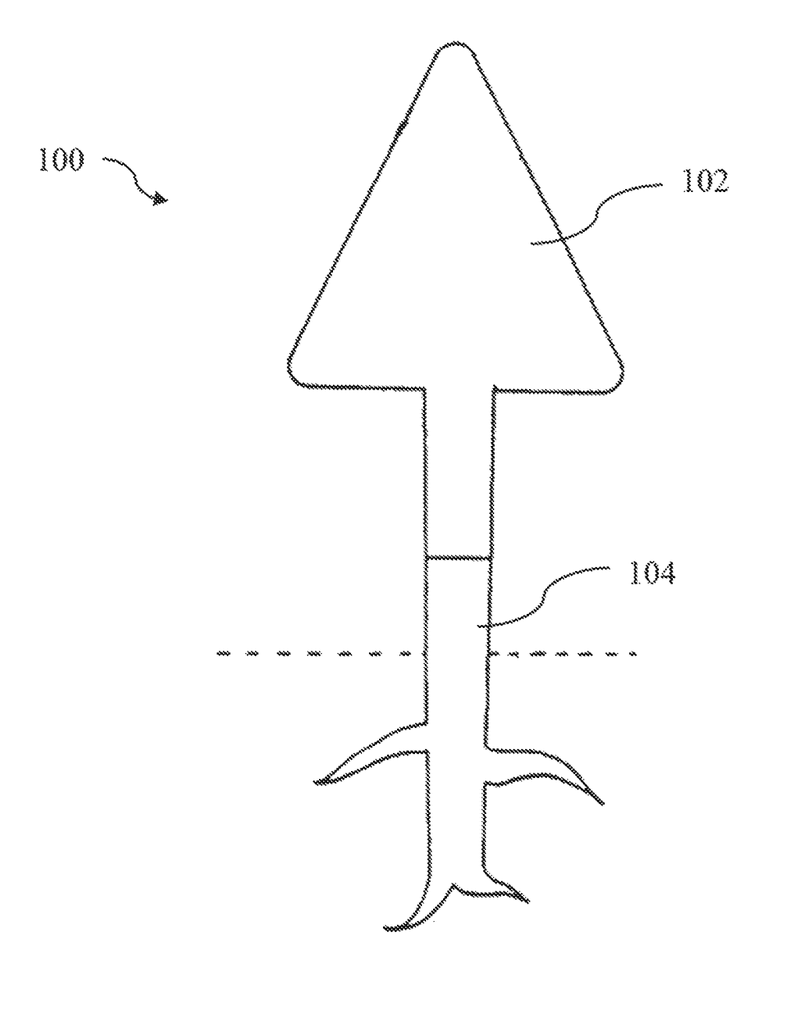
FIG. 1 is a schematic diagram of an example of a composite orange tree.

Referring to FIG. 1, a schematic diagram is shown of a composite orange tree 100 comprising a fruiting cultivar scion 102 grafted onto a citrus-greening resistant rootstock 104. The resulting composite orange tree 100 can demonstrate desired resistance to citrus greening. The composite orange tree 100 can be free or substantially free of one or more symptoms of the citrus-greening disease as described herein after being exposed to vectors of pathogens and/or pathogens which cause the citrus-greening disease. The composite orange tree 100 may be free or substantially free of one or more symptoms of the citrus-greening disease without or substantially without applying to the composite orange tree 100 treatment for the disease, including for example pesticide which treats or mitigates the disease. The pesticide may include one or more of insecticides (e.g., for impairing and/or killing psyllids which transmit the bacterium *Candidatus* Liberibacter *asiaticus*), bactericides (e.g., for impairing and/or killing the bacterium *Candidatus* Liberibacter *asiaticus*) and larvicides (e.g., for impairing and/or killing larvae of psyllids). The composite orange tree 100 may demonstrate desired resistance without having been contacted with a dosage regimen of pesticide sufficient to prevent, alleviate, and/or eliminate the citrus greening disease.

The composite orange tree 100 may be free or substantially free of all symptoms of the citrus greening disease without or substantially without being treated for the disease. For example, the composite orange tree 100 may be able to maintain desired productivity of sweet oranges, such that the composite orange tree 100 is a commercially viable sweet orange producing tree. The composite orange tree 100 can be resistant to the citrus greening disease such that it can produce a desired quantity of fruits which ripen into sweet oranges. The desired productivity and/or sweetness of fruits suited for commercial viability will be understood by a person of ordinary skill in the art.

The composite orange tree 100 may be free or substantially free of other symptoms of the citrus greening disease after exposure to pathogens which cause the disease, including asymmetric chlorosis, abnormal coloration of the peel, curvature of the central core, and/or bearing irregularly shaped fruits. For example, the peel of the ripened oranges produced by the composite orange tree 100 may be entirely orange in color and/or be free or substantially free of yellow coloring at the peduncle (stem) of the fruit. The central core of the ripened fruits may be free or substantially free of any curvature.

In some cases, the composite orange tree 100 is at least or about 20%, 25%, 30%, 35%, 40%, 50%, 60%, 70%, 80%, 90%, 95%, or more than 95% free of all symptoms of the citrus greening disease without or substantially without being treated for the disease. The composite orange tree 100 may be 100%, 95%, 90%, 85%, 80%, 75%, 70%, or 60% productive and able to maintain desired productivity of sweet oranges. Productivity of the composite orange tree may be compared to a composite orange tree not exposed to citrus greening disease. Productivity of the composite orange tree may be compared to an orange tree treated with a pesticide so as to be protected from citrus greening disease. Productivity of the composite orange tree may be compared to a cultivated orange tree not exposed to citrus greening disease. In some cases, productivity of the composite orange tree is compared to a composite orange tree not exposed to an environmental stress such as water having elevated salt content. In some cases, productivity of the composite tree is compared to a commercial orange tree that is non-resistant exposed or not exposed to citrus greening disease. In some cases, productivity of the composite tree is compared to a commercial orange tree that is non-resistant exposed or not exposed to an environmental stress.

In some cases, the composite orange tree 100 comprises a scion 102 that shows some symptoms of citrus greening disease grafted onto a citrus-greening resistant rootstock 104. The scion 102 can remain commercially viable despite showing symptoms of citrus greening disease. For example, the composite orange tree 100 maintains desired or commercially relevant production of sweet fruit. In some embodiments, the composite orange tree 100 can maintain desired productivity of sweet fruit about a year to about 5 years or more than 5 years after exposure to the citrus greening disease, including about 2 years, about 3 years or about 4 years, about 5 years or more than about 5 years. The composite tree 100 may remain commercially viable 1 year to about 5 years or more than about 5 years after exposure to the citrus greening disease, including about 2 years, about 3 years or about 4 years, about 5 years or more than about 5 years. In some embodiments, the composite orange tree 100 can produce commercially viable fruits without or substantially without use of pesticides which target citrus greening disease, or with use of a reduced quantity of such pesticides. In some embodiments, the composite orange tree 100 can produce commercially viable fruits with use of up to about 95%, about 90%, about 85%, about 80%, about 70%, or about 60% of the quantity of pesticides sufficient to treat commercial orange trees such that the commercial orange trees can maintain commercial viability, such as a standard quantity of pesticides. For example, a composite orange tree 100 which has not been treated with any pesticides or with a reduced quantity of pesticides can maintain productivity of sweet oranges after at least about 1 year, about 2 years, about 3 years, about 4 years, or about 5 years, after exposure to the citrus greening disease, such that the composite tree 100 is considered commercially viable. In some embodiments, the composite tree 100 may exhibit some symptoms of citrus greening disease while maintaining commercial viability after at least about 1 year, about 2 years, about 3 years, about 4 years, or about 5 years, after exposure to the citrus greening disease, without being treated with pesticides or with treatment of reduced quantities of pesticides.

In some cases, a composite citrus tree as described herein, such as the composite orange tree 100, can have desired resistance to water having elevated salt content. In some cases, a composite citrus tree has a desired resistance to brackish water. The composite citrus tree may have a rootstock which provides increased resistance to brackish water. For example, the rootstock 104 of the composite orange tree 100 may have resistance to brackish water such that the composite tree 100 can maintain commercial viability after exposure to brackish water and continue to produce sweet fruits of the scion 102 after the exposure. In some cases, a composite citrus tree can maintain commercial viability after exposure to brackish water for at least about 1 year, about 2 years, about 3 years, about 4 years or about 5 years. In some cases, the exposure to brackish water is for at least 1 day, at least 2 days, at least 3 days, at least 4 days, at least 5 days, at least 6 days, at least 7 days, at least 8 days, at least 9 days, at least 10 days, or at least a duration that is more than 10 days. In some cases, the exposure to brackish water is for at least 1 week, at least 2 weeks, at least 3 weeks, at least 4 weeks, at least 5 weeks, at least 6 weeks, at least 7 weeks, at least 8 weeks, at least 9 weeks, at least 10 weeks, or more than 10 weeks. In some cases, the exposure to brackish water is for about 1 week, about 2 weeks, about 3 weeks, about 4 weeks, about 5 weeks, about 6 weeks, about 7 weeks, about 8 weeks, about 9 weeks, about 10 weeks, or more than 10 weeks. In some instances, the exposure to brackish water is in a range of about 1 day to about 8 days, about 1 week to about 10 weeks, about 2 weeks to about 9 weeks, about 3 weeks to about 7 weeks, or about 4 weeks to about 6 weeks.

Symptoms of exposure to water with elevated salt content, such as brackish water, in plants which do have resistance to water with elevated salt content can include at least one of stunted growth, reduction in quantity of fruits produced, reduction in size of leaves, reduction in size of stems, reduction in size of roots, reduction in size of fruits, failure of buds to open and/or grow, death of tree branches, premature leaf fall color, and premature leaf drop. In some cases, symptoms can include at least one of leaf necrosis and marginal leaf burn. Symptoms may become evident in late summer following the growing season, or during and/or periods of hot and dry weather. In some cases, exposure of citrus trees which are not resistant to brackish water with elevated salt content can lead to death of the citrus trees.

In some cases, exposure of a composite citrus tree, such as the composite orange tree 100, to brackish water comprises growing the composite citrus tree at sea level without supplemental fresh water. In some cases, exposure of a composite citrus tree to brackish water comprises growing the composite citrus tree at sea level with a reduced fresh water watering regimen. For example, the reduced fresh water watering regimen would be insufficient to maintain commercial viability of a commercial citrus tree line, such as to maintain commercial viability for a same or similar period of time. A composite citrus tree as described herein can maintain commercial viability after growing at sea level for a period described herein without supplemental fresh water, or with a reduced fresh water watering regimen that would be insufficient to maintain commercial viability of a commercial citrus tree line for a same or similar period of time. In some cases, the reduced fresh water watering regimen is up to about 90% that of what one skilled in the art would administer to a corresponding commercial citrus tree, including up to about 85%, about 80%, about 75%, about 70%, about 60%. In some cases, the reduced fresh water watering regimen is about 50% or less that of what one skilled in the art would administer to a corresponding commercial citrus tree. In some cases, the corresponding commercial citrus tree may comprise a commercial citrus tree grown from its own rootstock, and/or a commercial citrus scion grafted onto a rootstock not resistant to brackish water.

Brackish water as described herein can have a salt content of about 1,000 ppm to about 35,000 ppm. For example, a composite citrus tree may be able to maintain commercial viability after exposure to water having a salt content of about 1,000 ppm to about 35,000 ppm. In some cases, the brackish water can have a salt content of about 1,000 ppm to about 5,000 ppm, including about 5,000 ppm to about 15,000 ppm, or about 15,000 ppm to about 35,000 ppm. In some cases, the brackish water can have a salt content of about 1,000 ppm to about 2,000 ppm, about 1,000 ppm to about 3,000 ppm, about 1,000 ppm to about 5,000 ppm, about 5,000 ppm to about 7,000 ppm, about 5,000 ppm to about 10,000 ppm, about 10,000 ppm to about 15,000 ppm, about 5,000 ppm to about 12,000 ppm, about 15,000 ppm to about 20,000 ppm, about 15,000 ppm to about 25,000 ppm, about 15,000 ppm to about 30,000 ppm, about 20,000 ppm to about 35,000 ppm, about 20,000 ppm to about 25,000 ppm, about 20,000 ppm to about 30,000 ppm, about 25,000 ppm to about 35,000 ppm, about 30,000 ppm to about 35,000 ppm, about 5,000 ppm to about 25,000 ppm, about 5,000 ppm to about 30,000 ppm, or about 5,000 ppm to about 35,000 ppm.

In some cases, a composite citrus tree, such as the composite orange tree 100, as described herein can demonstrate desired resistance to citrus greening as well as to growth in water having elevated salt content, such as brackish water.

Provided herein are composite citrus trees that have a desired resistance to stress due to flooding. Flooding may occur due to high rain falls, overbank flooding, flash flooding, ice jam flooding, or coastal flooding. In some cases, flooding is related to a hurricane, a tsunami, a high tide, a storm surge, or a tropical storm. The hurricane may be a category 1, category 2, category 3, category 4, or category 5 hurricane. In some cases, a composite citrus tree maintains commercial viability after a hurricane. In some cases, a composite citrus tree remains viable after a hurricane. In some cases, as a result of flooding a composite citrus tree as described herein may be exposed to flood water. The flood water may comprise fresh water, brackish water, saline water, or briny water. In some cases, the flood water comprises brackish water. The flood water may comprise chemicals, toxins, or infectious organisms. In some cases, a composite citrus tree maintains commercial viability after exposure to flood water for at least about 1 year, about 2 years, about 3 years, about 4 years or about 5 years. In some cases, the exposure to flood water is for at least or about 1 day, 2 days, 3 days, 4 days, 5 days, 6 days, 7 days, 8 days, 9 days, 10 days, or more than 10 days. In some cases, the exposure to flood water is for at least 1 week, at least 2 weeks, at least 3 weeks, at least 4 weeks, at least 5 weeks, at least 6 weeks, at least 7 weeks, at least 8 weeks, at least 9 weeks, at least 10 weeks, or more than 10 weeks. In some cases, the exposure to flood water is for about 1 week, about 2 weeks, about 3 weeks, about 4 weeks, about 5 weeks, about 6 weeks, about 7 weeks, about 8 weeks, about 9 weeks, about 10 weeks, or more than 10 weeks. In some instances, the exposure to flood water is in a range of about 1 day to about 8 days, about 1 week to about 10 weeks, about 2 weeks to about 9 weeks, about 3 weeks to about 7 weeks, or about 4 weeks to about 6 weeks.

Flood water comprising varying salt contents are differentially tolerated by plants of the disclosure herein. Flood water is tolerated having a salt content of about 50 ppm to about 50,000 ppm, such as a salt content of about 50 ppm, about 100 ppm, about 200 µm, about 500 ppm, about 1000 ppm, about 5000 ppm, about 10,000 ppm, about 15,000 ppm, about 20,000 ppm, about 25,000 ppm, about 30,000 ppm, about 40,000 ppm, or about 50,000 ppm. Flood water is tolerated having a salt content of about 50 ppm to about 50,000 ppm, such as a salt content of at least 50 ppm, at least 100 ppm, at least 200 pm, at least 500 ppm, at least 1000 ppm, at least 5000 ppm, at least 10,000 ppm, at least 15,000 ppm, at least 20,000 ppm, at least 25,000 ppm, at least 30,000 ppm, at least 40,000 ppm, or at least 50,000 ppm.

A composite citrus tree as described herein can demonstrate desired resistance to one or more stresses. For example, the composite tree demonstrates resistance to citrus greening as well as to growth in water having elevated salt content. In some instances, the one or more stresses is an abiotic stress. In some instances, the one or more stresses is a biotic stress. Exemplary stresses include stress due to bacteria, fungi, insect, heat, cold, drought, salinity, light, nutrient, wind, drought, climate event, high visible light, or combinations thereof. In some cases, the exposure to the one or more stresses is for at least or about 1 day, 2 days, 3 days, 4 days, 5 days, 6 days, 7 days, 8 days, 9 days, 10 days, or more than 10 days. In some cases, the exposure to the one or more stresses is for at least or about 1 week, 2 weeks, 3 weeks, 4 weeks, 5 weeks, 6 weeks, 7 weeks, 8 weeks, 9 weeks, 10 weeks, or more than 10 weeks. In some instances, the exposure to the one or more stresses is in a range of about 1 day to about 8 days, about 1 week to about 10 weeks, about 2 weeks to about 9 weeks, about 3 weeks to about 7 weeks, or about 4 weeks to about 6 weeks.

Plant performance of composite trees as described herein may be unaffected or improved despite exposure to one or more stresses. In some cases, plant performance is measured by productivity, survival, viability of fruiting parts, yield of fruiting parts, weight of fruiting parts, quality of fruiting parts (e.g., taste, size shape, color, or texture), resistance to pathogen infection and resultant symptoms, or resistance to stress due to heat, cold, drought, salinity, light, nutrient, wind, drought, climate event, or high visible light. In some instances, plant performance is measured by at least one of a reduction in fertilizer, herbicide, insecticide, and pesticide use without affecting yield. Reduction to fertilizer, herbicide, insecticide, or pesticide use may be determined by comparison to the industry use over ten years, to the state-wide average, or the national average. The reduction of fertilizer use may be at least 5%. In some cases, the reduction of fertilizer is in the range of about 5%-100%, 10%-90%, 20%-80%, 30%-70%, 40%-60%, 50%-95%, 65%-85%, or 75%-95%. In some instances, the reduction of herbicide use is at least 5%. In some cases, the reduction of herbicide is in the range of about 5%-100%, 10%-90%, 20%-80%, 30%-70%, 40%-60%, 50%-95%, 65%-85%, or 75%-95%. In some instances, the reduction of insecticide use is at least 5%. In some cases, the reduction of insecticide is in the range of about 5%-100%, 10%-90%, 20%-80%, 30%-70%, 40%-60%, 50%-95%, 65%-85%, or 75%-95%. In some instances, the reduction of pesticide use is at least 5%. In some cases, the reduction of pesticide is in the range of about 5%-100%, 10%-90%, 20%-80%, 30%-70%, 40%-60%, 50%-95%, 65%-85%, or 75%-95%.

Provided herein are composite trees, wherein the composite trees maintain their productivity or substantially maintain their productivity despite exposure to one or more stresses as compared to non-resistant trees In some cases, the productivity of the composite trees is unaffected or improved despite exposure to one or more stresses. In some cases, the survival of the composite trees is unaffected or improved despite exposure to one or more stresses. The productivity or survival of the composite trees may be maintained by about 5%-100%, 10%-90%, 20%-80%, 30%-70%, 40%-60%, 50%-95%, 65%-85%, or 75%-95%. In some cases, the productivity or survival of the composite trees are improved compared to non-resistant trees. For example, the productivity or survival of the composite trees are improved by at least about 4%, 5%, 6%, 7%, 8%, 9%, 10%, 11%, 12%, 13%, 14%, 15%, 16%, 17%, 18%, 19%, 20%, 25%, 30%, 35%, 40%, 45%, 50%, 55%, 60%, 65%, 70%, 75%, 80%, 85%, 90%, 95%, 99%, or 100% as compared to non-resistant trees.

The plant performance of a composite tree as described herein may be compared to a composite tree grown in absence of one or more stresses. In some cases, the plant performance of a composite tree is compared to a non-resistant tree grown in similar conditions. Similar conditions may be similar environment or similar growing conditions. Environmental factors include, but are not limited to, sun exposure, temperature, soil composition, soil moisture, wind, humidity, and soil pH. Growing conditions, include but are not limited to, amount of watering, amount of pesticide, amount of herbicide, amount of insecticide, duration of priming, duration of germination, and timing of sowing. In some instances, the stress-resistant composite tree is compared to a non-resistant tree grown at a same time. For example, the trees grown at the same time are grown on an adjacent or nearby field.

A number of fruiting cultivar scions 102 are consistent with the disclosure herein including various sweet orange producing cultivars. Scions for any of a number of sweet orange producing cultivars can be used together with the rootstock 104 to produce composite orange 100 trees which demonstrate desired resistance to the citrus greening disease and/or water with elevated salt content. The sweet orange producing cultivars may be susceptible to the citrus greening disease and/or cannot maintain commercial viability after exposure to water with elevated salt content. For example, the fruiting cultivar scion 102 may be sensitive to the citrus greening disease and/or brackish water if the cultivar scion is not grafted to the rootstock 104, such as when grown with its own rootstock. The fruiting cultivar scion 102 can be one or more cultivars selected from the group: Washington Navel, Valencia, Trovita, Hamlin, Shamouti, Parson Brown, Pineapple, Queen, Sunstar, Gardner, and Mid-Sweet, Blood Oranges, Lue Gim Gong, Rhode Island Valencia and/or the Homosassa.

A number of sources for the rootstock 104 are consistent with the disclosure herein. The citrus greening resistant rootstock 104 can be derived from a feral citrus greening resistant orange tree. The citrus greening resistant rootstock 104 can be derived from a cultivated citrus greening resistant orange tree. The citrus greening resistant rootstock 104 can be derived from a non-transgenic citrus greening resistant orange tree. The citrus greening resistant rootstock 104 can be derived from a transgenic citrus greening resistant orange tree. The citrus greening resistant rootstock 104 can be a rootstock derived from a seed of a feral or wild cultivar, and may be deposited in a public repository. The citrus greening resistant rootstock 104 can be a rootstock derived from a plant sharing an allele present in a seed of a feral or wild cultivar, and may be deposited in a public repository and where the allele is absent from the fruiting cultivar scion 102 grafted to the rootstock 104. The citrus greening resistant rootstock 104 can be a rootstock derived from a plant sharing an allele present in a seed of a feral or wild cultivar, where the allele is absent from the fruiting cultivar scion 102, and where the rootstock 104 is transgenic. In some cases, the citrus greening resistant rootstock 104 is resistant to brackish water.

The citrus greening resistant rootstock 104 can be a rootstock derived from a seed of a feral or wild cultivar. An exemplary seed stock is that deposited under ATCC Accession No. PTA-124301, although additional seed stocks are consistent with the present disclosure. The citrus greening resistant rootstock 104 can be a rootstock derived from a plant sharing an allele present in a seed of a feral or wild cultivar, such as that deposited under ATCC Accession No. PTA-124301 or other seed source and where the allele is absent from the fruiting cultivar scion 102 grafted to the rootstock 104. The citrus greening resistant rootstock 104 can be a rootstock derived from a plant sharing an allele present in a seed of a feral or wild cultivar, such as that deposited under ATCC Accession No. PTA-124301 or other seed source where the allele is absent from the fruiting cultivar scion 102, and where the rootstock 104 is transgenic. In some cases, the citrus greening resistant rootstock 104 is resistant to brackish water.

In some embodiments, seeds, seedlings, or plants descended from composite trees described herein are provided. In some cases, seeds, seedlings, or plants descended from composite trees described herein comprise resistance to citrus greening. In some cases, seeds, seedlings, or plants descended from composite trees as described herein are capable of growth in water having elevated salt content, such as brackish water. In some cases, seeds, seedlings, or plants descended from composite trees described herein comprise resistance to stress due to bacteria, fungi, insect, heat, cold, drought, salinity, light, nutrient, wind, drought, climate event, high visible light, or combinations thereof. In some cases, exposure to the stress is for at least or about 1 day, 2 days, 3 days, 4 days, 5 days, 6 days, 7 days, 8 days, 9 days, 10 days, or more than 10 days. In some cases, the exposure to the stress is for at least 1 week, at least 2 weeks, at least 3 weeks, at least 4 weeks, at least 5 weeks, at least 6 weeks, at least 7 weeks, at least 8 weeks, at least 9 weeks, at least 10 weeks, or more than 10 weeks. In some cases, the exposure to the stress is for about 1 week, about 2 weeks, about 3 weeks, about 4 weeks, about 5 weeks, about 6 weeks, about 7 weeks, about 8 weeks, about 9 weeks, about 10 weeks, or more than 10 weeks. In some instances, the exposure to the stress is in a range of about 1 day to about 8 days, about 1 week to about 10 weeks, about 2 weeks to about 9 weeks, about 3 weeks to about 7 weeks, or about 4 weeks to about 6 weeks.

Provided herein are seeds, seedlings, or plants descended from composite trees, wherein despite exposure to stress, the seeds, seedlings, or plants may comprise unaffected or improved plant performance. The plant performance of the seeds, seedlings, or plants descended from composite trees may be maintained by about 5%-100%, 10%-90%, 20%-80%, 30%-70%, 40%-60%, 50%-95%, 65%-85%, or 75%-95%. In some cases, the plant performance of the seeds, seedlings, or plants descended from composite trees is improved compared to seeds, seedlings, or plants descended from non-resistant trees. For example, the plant performance of the seeds, seedlings, or plants descended from composite trees are improved by at least 4%, 5%, 6%, 7%, 8%, 9%, 10%, 11%, 12%, 13%, 14%, 15%, 16%, 17%, 18%, 19%, 20%, 25%, 30%, 35%, 40%, 45%, 50%, 55%, 60%, 65%, 70%, 75%, 80%, 85%, 90%, 95%, 99%, or 100% as compared to seeds, seedlings, or plants descended from non-resistant trees. In some cases, plant performance of the seeds, seedlings, or plants descended from composite trees comprises size, dry weight, shoot dry weight, shoot fresh weight, shoot length, radical length, pigment production, leaf size, hypocotyl length, chlorophyll level, leaf area, root dry weight, productivity, survival, viability of fruiting parts, yield of fruiting parts, weight of fruiting parts, or quality of fruiting parts (e.g., taste, size shape, color, or texture).

Provided herein are seeds that provide starting material for composite trees. A number of seed sources are consistent with various embodiments of the disclosure herein. Some such seeds are deposited under ATCC Accession No. PTA-124301. In some cases, seeds disclosed herein such as those deposited under ATCC Accession No. PTA-124301, or other seed stock consistent with the disclosure herein yield resultant trees or rootstock exhibiting resistance to citrus greening disease. The seeds or resultant trees, or trees having rootstock from said seeds or sharing an allele in common with said seeds and absent from at least some commercial cultivars are in some cases capable of growth in water having elevated salt content, such as brackish water. The seeds or resultant trees, or trees having rootstock form said seeds or sharing an allele in common with said seeds and absent from at least some commercial cultivars are in some cases resistant to one or more stresses, wherein the stress is stress due to bacteria, fungi, insect, heat, cold, drought, salinity, light, nutrient, wind, drought, climate event, high visible light, or combinations thereof. In some cases, exposure to the stress or the citrus greening disease is for at least or about 1 day, 2 days, 3 days, 4 days, 5 days, 6 days, 7 days, 8 days, 9 days, 10 days, or more than 10 days. In some cases, exposure to the stress or the citrus greening disease is for at least 1 week, at least 2 weeks, at least 3 weeks, at least 4 weeks, at least 5 weeks, at least 6 weeks, at least 7 weeks, at least 8 weeks, at least 9 weeks, at least 10 weeks, or more than 10 weeks. In some cases, exposure to the stress or the citrus greening disease is for about 1 week, about 2 weeks, about 3 weeks, about 4 weeks, about 5 weeks, about 6 weeks, about 7 weeks, about 8 weeks, about 9 weeks, about 10 weeks, or more than 10 weeks. In some instances, the exposure to the stress is in a range of about 1 day to about 8 days, about 1 week to about 10 weeks, about 2 weeks to about 9 weeks, about 3 weeks to about 7 weeks, or about 4 weeks to about 6 weeks.

The seeds or resultant trees, or trees having rootstock from said seeds or sharing an allele in common with said seeds and absent from at least some commercial cultivars in some cases require less pesticide, herbicide, fertilizer, insecticide, and/or antibiotic. For example, resultant trees produce commercially viable fruits without or substantially without use of pesticides which target citrus greening disease, or with use of a reduced quantity of such pesticides. In some embodiments, resultant trees produce commercially viable fruits with use of up to about 95%, about 90%, about 85%, about 80%, about 70%, or about 60% of the quantity of pesticides sufficient to treat commercial orange trees such that the commercial orange trees can maintain commercial viability, such as a standard quantity of pesticides. In some embodiments, resultant trees produce commercially viable fruits with use of up to about 95%, about 90%, about 85%, about 80%, about 70%, or about 60% of the quantity of insecticides sufficient to treat commercial orange trees such that the commercial orange trees can maintain commercial viability, such as a standard quantity of insecticides. In some embodiments, resultant trees produce commercially viable fruits with use of up to about 95%, about 90%, about 85%, about 80%, about 70%, or about 60% of the quantity of antibiotic sufficient to treat commercial orange trees such that the commercial orange trees can maintain commercial viability, such as a standard quantity of antibiotic.

In some embodiments, resultant trees from seeds as disclosed herein, such as trees derived from ATCC Accession No. PTA-124301, are commercially viable. In some embodiments, resultant trees remain commercially viable despite exposure to stress. The stress may be caused by a pathogen such as the pathogen that causes citrus greening disease. In some cases, the stress results from growth in water having elevated salt content. In some cases, the stress results from bacteria, fungi, insect, heat, cold, drought, salinity, light, nutrient, wind, drought, climate event, high visible light, or combinations thereof. In some cases, resultant trees maintain their productivity or substantially maintain their productivity despite exposure to stress. In some cases, the productivity of resultant trees is unaffected or improved despite exposure to stress. In some cases, the survival of resultant trees is unaffected or improved despite exposure to stress. The productivity or survival of resultant trees may be maintained by about 5%-100%, 10%-90%, 20%-80%, 30%-70%, 40%-60%, 50%-95%, 65%-85%, or 75%-95%. The productivity or commercial viability, productivity, or survival of resultant trees may be compared to resultant trees from seeds of non-resistant trees. For example, the productivity or survival of resultant trees may be unaffected or improved by at least about 4%, 5%, 6%, 7%, 8%, 9%, 10%, 11%, 12%, 13%, 14%, 15%, 16%, 17%, 18%, 19%, 20%, 25%, 30%, 35%, 40%, 45%, 50%, 55%, 60%, 65%, 70%, 75%, 80%, 85%, 90%, 95%, 99%, or 100% as compared to resultant trees from seeds of non-resistant trees. The resultant trees may be free or substantially free of other symptoms of the citrus greening disease after exposure to pathogens which cause the disease, including asymmetric chlorosis, abnormal coloration of the peel, curvature of the central core, and/or bearing irregularly shaped fruits as compared to resultant trees from seeds of non-resistant trees. In some cases, resultant trees retain commercial viability despite having symptoms of citrus greening disease as compared to resultant trees from seeds of non-resistant trees having symptoms of citrus greening disease.

In some embodiments, a citrus greening resistant transgenic plant is provided, the plant comprising a cell of a citrus greening sensitive citrus plant into which a mutation is introduced, the mutation mimicking an allele present in a seed of a feral or wild cultivar and absent in a non-transgenic citrus greening sensitive citrus plant. The allele can be present in the genomic sequence of a feral or wild cultivar while being absent from commercially grown orange lines. In some embodiments, the mutation introduced into the transgenic plant is a point mutation. In some embodiments, the mutation is introduced through TILLING (Targeting Induced Local Lesions in Genomes). In TILLING, mutagenesis is combined with screening of the DNA to identify mutations in a target gene. TILLING can then be used to identify mutants that have a modified function in plants. For example, mutants are screened for at least one of increasing viability, increasing productivity, and decreasing citrus-greening disease symptoms in citrus plants following citrus greening disease exposure.

In some embodiments, the mutation is introduced through site-directed mutagenesis. Site-directed mutagenesis, typically utilizes a synthetic DNA primer. This synthetic primer contains the desired mutation and is complementary to the template DNA around the mutation site so that it can hybridize with the DNA in the gene of interest. The mutation may be a single base change (a point mutation), multiple base changes, deletion, insertion, or a combination thereof. The single-strand primer is then extended using a DNA polymerase, which copies the rest of the gene. The copied gene contains the mutated site, and may then be introduced into a plant cell. Mutants exhibiting desired plant traits can be selected. The DNA of the mutants can be sequenced to identify the mutant allele.

In some embodiments, the mutation is introduced using CRISPR/Cas9. Cas9, when expressed or transfected in cells alongside a gRNA, allows for the targeted introduction or deletion of genetic information via a complex with a Clustered Regularly Interspaced Short Palindromic Repeats (CRISPR) sequence of mRNA. In a CRISPR/Cas9 process, a gRNA shepherds the Cas9 enzyme to a specific stretch of DNA. Cas9 then cleaves the DNA to disable or repair a gene. Cas9 can be delivered to a plant cell by a virus (e.g. DNA virus or RNA virus). CRISPR/Cas9 system can then be used to identify genes that affect a citrus plant's susceptibility to citrus-greening disease.

The mutation may comprise a transgene. The mutation may comprise a copy of a coding region of said allele present in a feral or wild cultivar that may be deposited in a public repository or sequenced such that its sequence is publicly available, while absent in a non-transgenic citrus-greening sensitive citrus plant.

In some cases, a citrus greening resistant transgenic plant as described herein can demonstrate desired resistance to brackish water.

In some embodiments, a composite citrus plant provided herein may comprise at least one first allele present in a commercially grown orange line and absent in a feral or wild cultivar and at least one second allele absent in the commercially grown orange line and present in a feral or wild cultivar. The commercially grown orange line may be any one of the fruiting cultivars described herein, including for example, the Washington Navel, Valencia, Trovita, Hamlin, Shamouti, Parson Brown, Pineapple, Queen, Sunstar, Gardner, and Mid-Sweet, Blood Oranges, Lue Gim Gong, Rhode Island Valencia and/or the Homosassa. The citrus plant may resemble the commercially grown orange line at least about 75% of loci, including at least about 87%, and at least about 93%, where the commercially grown orange line differs from a feral or wild cultivar. The citrus plant of may be transgenic. In some embodiments, the citrus plant may be a hybrid. The citrus plant may be a descendent of a plant of a feral or wild cultivar.

In some cases, a composite citrus tree as provided herein can have at least one allele common to a feral or wild cultivar and absent from at least one commercial citrus tree line. In some cases, a composite citrus tree can have at least about 50%, at least about 75%, at least about 87%, or at least about 93% of alleles as that of a commercially grown citrus tree.

A method of growing a composite orange tree as described herein can include grafting a fruiting cultivar scion which provides the desired sweet orange fruit to a citrus greening disease resistant rootstock. The citrus greening disease resistant rootstock can have one or more characteristics as described herein. Grafting of the fruiting cultivar scion can be performed according to one or more processes known to one skilled in the art. The fruiting cultivar scion can be selected based on various characteristics of the fruiting cultivar, including a desired productivity of the cultivar and/or sweetness of fruits produced by the cultivar. The fruiting cultivar scion may be a high-yield cultivar. For example, the fruiting cultivar scion may be one or more commercially available cultivars as described herein.

A method of generating a citrus greening resistant composite orange tree may include mutagenizing at least one citrus plant cell having an allele present in a feral or wild cultivar and absent from a citrus greening sensitive citrus plant. The citrus greening sensitive citrus plant may include one or more commercially available cultivars, such as one or more fruiting cultivars as described herein.

Described herein, in certain embodiments, are orange seeds derived from composite trees comprising resistant rootstocks of seeds that were deposited on Jul. 20, 2017 with the American Type Culture Collection (ATCC; an International Depositary Authority), Manassas, VA, USA, and assigned ATTC Patent Deposit Designation number PTA-124301. This deposit was made under the provisions of the Budapest Treaty on the International Recognition of the Deposit of Microorganisms for the Purpose of Patent Procedure and the Regulations (Budapest Treaty).

Described herein are composite trees comprising citrus-greening resistant rootstocks. In some embodiments, the citrus greening resistant rootstock may be derived from a feral citrus greening resistant orange tree. The citrus greening resistant rootstock may be derived from a cultivated citrus greening resistant orange tree. The citrus greening resistant rootstock may be derived from a non-transgenic citrus greening resistant orange tree. The citrus greening resistant rootstock may be derived from a transgenic citrus greening resistant orange tree. The citrus greening resistant rootstock may be a rootstock derived from a seed of a feral or wild cultivar, and may be deposited in a public repository. The citrus greening resistant rootstock may be a rootstock derived from a plant sharing an allele present in a seed of a feral or wild cultivar, and may be deposited in a public repository and where the allele is absent from the fruiting cultivar scion grafted to the rootstock. The citrus greening resistant rootstock may be a rootstock derived from a plant sharing an allele present in a seed of a feral or wild cultivar, where the allele is absent from the fruiting cultivar scion, and where the rootstock is transgenic. One such rootstock is derived from seeds deposited under ATCC Accession No. PTA-124301, although alternatives are also contemplated herein. In some cases, the citrus greening resistant rootstock is resistant to brackish water. The citrus greening resistant rootstock may be resistant to citrus greening despite exposure to a citrus greening disease bacterium or citrus greening disease vector. In some cases, the exposure to the citrus greening disease bacterium or citrus greening disease vector is for at least or about 1 day, 2 days, 3 days, 4 days, 5 days, 6 days, 7 days, 8 days, 9 days, 10 days, or more than 10 days. In some cases, the exposure to the citrus greening disease bacterium or citrus greening disease vector is for at least or about 1 week, 2 weeks, 3 weeks, 4 weeks, 5 weeks, 6 weeks, 7 weeks, 8 weeks, 9 weeks, 10 weeks, or more than 10 weeks. In some instances, the exposure to the citrus greening disease bacterium or citrus greening disease vector is in a range of about 1 day to about 8 days, about 1 week to about 10 weeks, about 2 weeks to about 9 weeks, about 3 weeks to about 7 weeks, or about 4 weeks to about 6 weeks.

Described herein are composite trees comprising rootstocks resistant to one or more stresses. Exemplary stresses include stress due to bacteria, fungi, insect, heat, cold, drought, salinity, light, nutrient, wind, drought, climate event, high visible light, or combinations thereof. The resistant rootstocks may be resistant to exposure to one or more stresses. In some cases, the exposure to the one or more stresses is for at least or about 1 day, 2 days, 3 days, 4 days, 5 days, 6 days, 7 days, 8 days, 9 days, 10 days, or more than 10 days. In some cases, the exposure to the one or more stresses is for at least or about 1 week, 2 weeks, 3 weeks, 4 weeks, 5 weeks, 6 weeks, 7 weeks, 8 weeks, 9 weeks, 10 weeks, or more than 10 weeks. In some instances, the exposure to the one or more stresses is in a range of about 1 day to about 8 days, about 1 week to about 10 weeks, about 2 weeks to about 9 weeks, about 3 weeks to about 7 weeks, or about 4 weeks to about 6 weeks. One such rootstock is derived from seeds deposited under ATCC Accession No. PTA-124301, although alternatives are also contemplated herein.

Described herein, in certain embodiments, are resultant trees that have desired resistance. In some cases, the resultant trees, such as trees derived through hybridization, grafting or mutagenesis so as to be related to trees derived from a suitable source such as from orange seeds deposited under ATCC Accession No. PTA-124301 or other source as contemplated herein comprise resistance to citrus greening disease. The resultant trees may be capable of growth in water having elevated salt content, such as brackish water. In some cases, resultant trees comprise resistance to one or more stresses, wherein the stress is stress due to bacteria, fungi, insects, heat, cold, drought, salinity, light, nutrient, wind, drought, climate event, high visible light, or combinations thereof. In some cases, exposure to the stress or the citrus greening disease is for at least or about 1 day, 2 days, 3 days, 4 days, 5 days, 6 days, 7 days, 8 days, 9 days, 10 days, or more than 10 days. In some cases, exposure to the stress or the citrus greening disease is for at least 1 week, at least 2 weeks, at least 3 weeks, at least 4 weeks, at least 5 weeks, at least 6 weeks, at least 7 weeks, at least 8 weeks, at least 9 weeks, at least 10 weeks, or more than 10 weeks. In some cases, exposure to the stress or the citrus greening disease is for about 1 week, about 2 weeks, about 3 weeks, about 4 weeks, about 5 weeks, about 6 weeks, about 7 weeks, about 8 weeks, about 9 weeks, about 10 weeks, or more than 10 weeks. In some instances, the exposure to the stress is in a range of about 1 day to about 8 days, about 1 week to about 10 weeks, about 2 weeks to about 9 weeks, about 3 weeks to about 7 weeks, or about 4 weeks to about 6 weeks.

Resultant trees from orange seeds described herein may require less pesticide, herbicide, fertilizer, insecticide, and/or antibiotic treatment. For example, resultant trees produce commercially viable fruits without or substantially without use of pesticides which target citrus greening disease, or with use of a reduced quantity of such pesticides. In some embodiments, resultant trees produce commercially viable fruits with use of up to about 95%, about 90%, about 85%, about 80%, about 70%, or about 60% of the quantity of pesticides sufficient to treat commercial orange trees such that the commercial orange trees can maintain commercial viability, such as a standard quantity of pesticides. In some embodiments, resultant trees produce commercially viable fruits with use of up to about 95%, about 90%, about 85%, about 80%, about 70%, or about 60% of the quantity of insecticides sufficient to treat commercial orange trees such that the commercial orange trees can maintain commercial viability, such as a standard quantity of insecticides. In some embodiments, resultant trees produce commercially viable fruits with use of up to about 95%, about 90%, about 85%, about 80%, about 70%, or about 60% of the quantity of antibiotic sufficient to treat commercial orange trees such that the commercial orange trees can maintain commercial viability, such as a standard quantity of antibiotic.

In some embodiments, resultant trees are commercially viable. In some embodiments, resultant trees remain commercially viable despite exposure to stress. The stress may be caused by a pathogen such as the pathogen that causes citrus greening disease. In some cases, the stress results from growth in water having elevated salt content. In some cases, the stress results from bacteria, fungi, insect, heat, cold, drought, salinity, light, nutrient, wind, drought, climate event, high visible light, or combinations thereof. In some cases, resultant trees maintain their productivity or substantially maintain their productivity despite exposure to stress. In some cases, the productivity of resultant trees from seeds deposited under ATCC Accession No. PTA-124301 is unaffected or improved despite exposure to stress. In some cases, the survival of resultant trees is unaffected or improved despite exposure to stress. The productivity or survival of resultant trees may be maintained by about 5%-100%, 10%-90%, 20%-80%, 30%-70%, 40%-60%, 50%-95%, 65%-85%, or 75%-95%. The productivity or commercial viability, productivity, or survival of resultant trees may be compared to resultant trees from seeds of non-resistant trees. For example, the productivity or survival of resultant trees may be unaffected or improved by at least about 4%, 5%, 6%, 7%, 8%, 9%, 10%, 11%, 12%, 13%, 14%, 15%, 16%, 17%, 18%, 19%, 20%, 25%, 30%, 35%, 40%, 45%, 50%, 55%, 60%, 65%, 70%, 75%, 80%, 85%, 90%, 95%, 99%, or 100% as compared to resultant trees from seeds of non-resistant trees. The resultant trees may be free or substantially free of other symptoms of the citrus greening disease after exposure to pathogens which cause the disease, including asymmetric chlorosis, abnormal coloration of the peel, curvature of the central core, and/or bearing irregularly shaped fruits as compared to resultant trees from seeds of non-resistant trees. In some cases, resultant trees retain commercial viability despite having symptoms of citrus greening disease as compared to resultant trees from seeds of non-resistant trees having symptoms of citrus greening disease.

Definitions

As used herein, "citrus greening resistant" in the context of a citrus plant refers to a citrus plant that yields fruit that are not impacted, unaffected, not commercially impacted, and/or remain commercially viable after exposure to a citrus greening pathogen prior to and/or during fruit development, even in the absence or substantial absence of pesticide, herbicide, and/or antibiotic that conveys resistance to citrus greening, for example by killing the citrus greening pathogen, inhibiting progression of the disease, inhibiting pathogen growth, and/or inhibiting pathogen transmission. In some cases such a fruit retains a flavor that is sweet or unaffected by the bitter taste characteristic of citrus greening affected citrus plants, does not exhibit a green lower-half or stylar end, and/or otherwise retains commercial viability. In some cases a citrus greening resistant citrus plant is not infected when contacted to a citrus greening pathogen. Alternately, in some cases a citrus greening-resistant plant retains viability even after long-term exposure or long-term infection by a citrus greening pathogen.

"Commercially viable" as used herein is used to describe citrus trees, such as orange trees, which demonstrate characteristics which would be considered by a person skilled in the art as being suitable for commercial production purposes. For example, the quantity, appearance (e.g., coloration, size, and/or shape), and sweetness of fruits borne by a commercially viable orange tree would be that considered to be suitable for commercial production by one skilled in the art.

"Productivity" as used herein refers to the ability of a citrus tree, such as an orange tree, to bear fruits in the number, appearance (e.g., coloration, size and/or shape) and sweetness as would be considered to be suited for commercial productions purposes by one skilled in the art.

"TILLING" as used herein comprises introduction of mutations, even random mutations, and then screening for mutations, exhibited as mismatch complexes in heteroduplex DNA, in the mutagenized resultant DNA. Various embodiments of TILLING are described as comprising mutagenesis, for example using a chemical mutagen such as Ethyl methanesulfonate (EMS), ethidium bromide, or other point mutant, with a DNA screening-technique, such as a technique that identifies mutations such as insertions, deletions or single base mutations (also called point mutations) in a gene or locus of interest. Some embodiments of the method rely on the formation and detection of DNA heteroduplexes that result when multiple alleles are annealed, such as during or resulting from PCR, and are then melted and slowly cooled. A "bubble" forms at the mismatch position of two DNA strands differing at a single position. In some embodiments the bubble is then cleaved by a single stranded nuclease. The products are then separated by size, using any of a number of approaches. The presence of size variation represented by the cleavage products indicates the presence of allelic variation in the target locus. Mismatches may be due to induced mutation, heterozygosity within an individual, or natural variation between individuals.

"CRISPR" as used herein, refers to a system of targeted mutagenesis derived from a eubacterial and archaeal bacterial defense system. A CRISPR system comprising a nuclease complexed with a synthetic guide RNA (gRNA) is introduced into a cell, such that the cell's genome or other nucleic acids can be cut at a desired location, thereby introducing deletions, frame-shifts or other mutations into a locus.

As used herein, a plant is "feral" if it is a "volunteer" or otherwise is an unplanted, naturally occurring individual or specimen. Alternately, a plant is "cultivated" if it is found in a crop environment, is maintained for agricultural or other commercial use, or arose from human effort in its original germination or growth. Cultivated plants are in some cases planted and maintained through human effort throughout their lifespans, while in other cases cultivated plants are planted through human effort and are allowed to grow at least through part of their lives without human maintenance or effort.

A hybrid plant as used herein is a plant descending from parents having different genotypes, such as different genotypes conveying different traits. In some cases, the hybrid inherits beneficial traits from each patent not present in the other parent.

A plant or cell is "transgenic" as described herein when it comprises a nucleic acid segment not present in a nearest unmodified relative, or not present in the same locus and orientation in a nearest unmodified relative.

A number of approaches are known for identifying an allele or alleles that convey a desired trait such as resistance to citrus greening. For example, a genome of a resistant plant is sequenced and compared to at least one non-resistant relative. In some cases the lines are distinct at a plurality of loci, while in other cases the lines differ at a few or only one locus, such as 'near isogenic lines'.

Alleles are identified biochemically by assessing activity of the encoded factor, transgenically by introducing the allele or a mutation mimicking the allele into an otherwise sensitive line, by knocking out the allele and observing loss of resistance, by observing cosegregation of the allele and the trait, such as resistance to citrus greening, or by a combination of these approaches.

As used herein, a mutation mimics an allele if it conveys a similar structural or functional change, or results in a similar effect, as an allele or set of alleles that correspond with or result in citrus greening resistance.

The term "about" a number as used herein means a range spanning from 10% below the number to 10% above the number. The term "about" a range as used herein may also refer to a range 10% below the lowest value of the listed range up to 10% above the highest value of the listed range.

Numbered Embodiments

The disclosure is further elucidated by reference to the numbered embodiments herein. Numbered embodiment 1 comprises a composite orange tree comprising a fruiting cultivar scion grafted to a citrus-greening resistant rootstock. Numbered embodiment 2 comprises the composite orange tree of numbered embodiment 1 comprising a plurality of ripe orange fruit. Numbered embodiment 3 comprises the composite orange tree of numbered embodiments 1-2, wherein the ripe orange fruit have a sweet taste when ripe. Numbered embodiment 4 comprises the composite orange tree of numbered embodiments 1-3, wherein the ripe orange fruit have an orange color on their entire surface. Numbered embodiment 5 comprises the composite orange tree of numbered embodiments 1-4, wherein the citrus-greening resistant rootstock is derived from a feral citrus-greening resistant orange tree. Numbered embodiment 6 comprises the composite orange tree of numbered embodiments 1-5, wherein the citrus-greening resistant rootstock is derived from a cultivated citrus-greening resistant orange tree. Numbered embodiment 7 comprises the composite orange tree of numbered embodiments 1-6, wherein the citrus-greening resistant rootstock is derived from a non-transgenic citrus-greening resistant orange tree. Numbered embodiment 8 comprises the composite orange tree of numbered embodiments 1-7, wherein the citrus-greening resistant rootstock is derived from a transgenic citrus-greening resistant orange tree. Numbered embodiment 9 comprises the composite orange tree of numbered embodiments 1-8, wherein the citrus-greening resistant rootstock is a rootstock derived from a seed of a feral or wild cultivar exhibiting citrus-greening resistance, and wherein the seed is deposited under ATCC Accession No. PTA-124301. Numbered embodiment 10 comprises the composite orange tree of numbered embodiments 1-9, wherein the citrus-greening resistant rootstock is a rootstock derived from a plant sharing an allele present in a seed of a feral or wild cultivar exhibiting citrus-greening resistance, wherein the seed is deposited under ATCC Accession No. PTA-124301 and wherein the allele is absent from the fruiting cultivar. Numbered embodiment 11 comprises the composite orange tree of numbered embodiments 1-10, wherein the citrus-greening resistant rootstock is a rootstock derived from a plant sharing an allele present in a seed of a feral or wild cultivar exhibiting citrus-greening resistance, wherein the seed is deposited under ATCC Accession No. PTA-124301, wherein the allele is absent from the fruiting cultivar, and wherein the rootstock is transgenic. Numbered embodiment 12 comprises the composite orange tree of numbered embodiments 1-11, wherein the composite orange tree is not contacted to pesticide under a dosage regimen sufficient to prevent citrus greening. Numbered embodiment 13 comprises the composite orange tree of numbered embodiments 1-12, wherein the composite orange tree is contacted to a citrus greening disease bacterium. Numbered embodiment 14 comprises the composite orange tree of numbered embodiments 1-13, wherein the composite orange tree is contacted to a citrus greening disease vector. Numbered embodiment 15 comprises a method of generating a citrus-greening resistant orange tree, comprising mutagenizing at least one citrus plant cell having an allele present in a feral or wild cultivar exhibiting citrus-greening resistance and absent from a citrus-greening sensitive citrus plant. Numbered embodiment 16 comprises the method of numbered embodiments 1-15 comprising contacting the citrus plant having said allele to at least one citrus-greening bacterium. Numbered embodiment 17 comprises the method of numbered embodiments 1-16 comprising grafting a rootstock comprising said at least one citrus plant cell to a high yield citrus scion. Numbered embodiment 18 comprises the method of growing a citrus fruit in a citrus-greening environment comprising grafting a fruiting cultivar to a citrus-greening resistant rootstock. Numbered embodiment 19 comprises the method of numbered embodiments 1-18, wherein the citrus fruit have a sweet taste when ripe. Numbered embodiment 20 comprises the method of numbered embodiments 1-19, wherein the citrus fruit has an orange color on its lower surface. Numbered embodiment 21 comprises the method of numbered embodiments 1-20, wherein the citrus-greening resistant rootstock is derived from a feral citrus-greening resistant orange tree. Numbered embodiment 22 comprises the method of numbered embodiments 1-21, wherein the citrus-greening resistant rootstock is derived from a cultivated citrus-greening resistant orange tree. Numbered embodiment 23 comprises the method of numbered embodiments 1-22, wherein the citrus-greening resistant rootstock is derived from a non-transgenic citrus-greening resistant orange tree. Numbered embodiment 24 comprises the method of numbered embodiments 1-23, wherein the citrus-greening resistant rootstock is derived from a transgenic citrus-greening resistant orange tree. Numbered embodiment 25 comprises the method of numbered embodiments 1-24, wherein the citrus-greening resistant rootstock is a rootstock derived from a seed of a feral or wild cultivar exhibiting citrus-greening resistance, and wherein the seed is deposited under ATCC Accession No. PTA-124301. Numbered embodiment 26 comprises the method of numbered embodiments 1-25, wherein the citrus-greening resistant rootstock is a rootstock derived from a plant sharing an allele present in a seed of a feral or wild cultivar exhibiting citrus-greening resistance, wherein the seed is deposited under ATCC Accession No. PTA-124301, and wherein the allele is absent from the fruiting cultivar. Numbered embodiment 27 comprises the method of numbered embodiments 1-26, wherein the citrus-greening resistant rootstock is a rootstock derived from a plant sharing an allele present in a seed of a feral or wild cultivar exhibiting citrus-greening resistance, wherein the seed is deposited under ATCC Accession No. PTA-124301, wherein the allele is absent from the fruiting cultivar, and wherein the rootstock is transgenic. Numbered embodiment 28 comprises the method of numbered embodiments 1-27, wherein the composite orange tree is not contacted to pesticide under a dosage regimen sufficient to prevent citrus greening. Numbered embodiment 29 comprises the method of numbered embodiments 1-28, wherein the composite orange tree is contacted to a citrus greening disease bacterium. Numbered embodiment 30 comprises the method of numbered embodiments 1-29, wherein the composite orange tree is contacted to a citrus greening disease vector. Numbered embodiment 31 comprises a citrus-greening resistant transgenic plant, comprising a cell of a citrus-greening sensitive citrus plant into which a mutation is introduced, said mutation mimicking an allele present in a feral or wild cultivar exhibiting citrus-greening resistance and absent in a non-transgenic citrus-greening sensitive citrus plant. Numbered embodiment 32 comprises a citrus-greening resistant transgenic plant of numbered embodiments 1-31, wherein said allele is present in genomic sequence of a feral or wild cultivar exhibiting citrus-greening resistance and is absent from commercially grown orange lines. Numbered embodiment 33 comprises a citrus-greening resistant transgenic plant of numbered embodiments 1-32, wherein said mutation is a point mutation. Numbered embodiment 34 comprises a citrus-greening resistant transgenic plant of numbered embodiments 1-33, wherein said mutation is introduced through TILLING. Numbered embodiment 35 comprises a citrus-greening resistant transgenic plant of numbered embodiments 1-34, wherein said mutation is introduced through sequence—specific mutagenesis. Numbered embodiment 36 comprises a citrus-greening resistant transgenic plant of numbered embodiments 1-35, wherein said mutation is introduced through CRISPR. Numbered embodiment 37 comprises a citrus-greening resistant transgenic plant of numbered embodiments 1-36, wherein said mutation comprises a transgene. Numbered embodiment 38 comprises a citrus-greening resistant transgenic plant of numbered embodiments 1-37, wherein said mutation comprises a copy of a coding region of said allele present in a feral or wild cultivar exhibiting citrus-greening resistance and absent in a non-transgenic citrus-greening sensitive citrus plant. Numbered embodiment 39 comprises a citrus plant comprising at least one first allele present in commercially grown orange lines and absent in a feral or wild cultivar exhibiting citrus-greening resistance and at least one second allele absent in commercially grown orange lines and present in a feral or wild cultivar exhibiting citrus-greening resistance. Numbered embodiment 40 comprises a citrus plant of numbered embodiments 1-39, wherein said citrus plant resembles commercially grown orange lines at least 75% of loci where commercially grown orange lines differs from a feral or wild cultivar exhibiting citrus-greening resistance. Numbered embodiment 41 comprises a citrus plant of numbered embodiments 1-40, wherein said citrus plant resembles commercially grown orange lines at least 87% of loci where commercially grown orange lines differs from a feral or wild cultivar exhibiting citrus-greening resistance. Numbered embodiment 42 comprises a citrus plant of numbered embodiments 1-41, wherein said citrus plant resembles commercially grown orange lines at least 87% of loci where commercially grown orange lines differs from a feral or wild cultivar exhibiting citrus-greening resistance. Numbered embodiment 43 comprises a citrus plant of numbered embodiments 1-42, wherein said citrus plant resembles commercially grown orange lines at least 93% of loci where commercially grown orange lines differs from a feral or wild cultivar exhibiting citrus-greening resistance. Numbered embodiment 44 comprises a citrus plant of numbered embodiments 1-43, wherein said citrus plant is transgenic. Numbered embodiment 45 comprises a citrus plant of numbered embodiments 1-44, wherein said citrus plant is a hybrid. Numbered embodiment 46 comprises a citrus plant of numbered embodiments 1-45, wherein said citrus plant descends from a plant of a feral or wild cultivar exhibiting citrus-greening resistance. Numbered embodiment 47 comprises a citrus plant that yields commercially viable fruit following exposure to citrus greening disease, wherein the plant is exposed to a pesticide level insufficient to protect a citrus-greening sensitive plant. Numbered embodiment 48 comprises a citrus plant of numbered embodiments 1-46, wherein the plant is a graft. Numbered embodiment 49 comprises a citrus plant of numbered embodiments 1-48, wherein the plant is a hybrid. Numbered embodiment 50 comprises a citrus plant of numbered embodiments 1-49, wherein root tissue of the citrus plant comprises an allele absent from a citrus plant sensitive to the citrus greening disease. Numbered embodiment 51 comprises a citrus plant of numbered embodiments 1-50, wherein root tissue of the citrus plant comprises an allele present in a feral or wild cultivar exhibiting citrus-greening resistance and absent from a citrus plant sensitive to the citrus greening disease. Numbered embodiment 52 comprises a citrus plant of numbered embodiments 1-51, wherein root tissue of the citrus plant comprises an allele present in a feral or wild cultivar exhibiting citrus-greening resistance and root tissue is derived from a feral or wild cultivar exhibiting citrus-greening resistance. Numbered embodiment 53 comprises a citrus plant of numbered embodiments 1-52, wherein the pesticide level is zero. Numbered embodiment 54 comprises a citrus plant of numbered embodiments 1-53, wherein the plant yields commercially viable fruit at least 1 year after exposure to the citrus-greening disease. Numbered embodiment 55 comprises a citrus plant that requires no more than 50% of standard pesticide amount to yield commercially viable fruit following exposure to citrus greening disease. Numbered embodiment 56 comprises a citrus plant of numbered embodiments 1-55, wherein the plant is a graft. Numbered embodiment 57 comprises a citrus plant of numbered embodiments 1-56, wherein the plant is a hybrid. Numbered embodiment 58 comprises a citrus plant of numbered embodiments 1-57, wherein root tissue of the citrus plant comprises an allele absent from a citrus plant sensitive to the citrus greening disease. Numbered embodiment 59 comprises a citrus plant of numbered embodiments 1-58, wherein root tissue of the citrus plant comprises an allele present in a feral or wild cultivar exhibiting citrus-greening resistance and absent from a citrus plant sensitive to the citrus greening disease. Numbered embodiment 60 comprises a citrus plant of numbered embodiments 1-59, wherein root tissue of the citrus plant comprises an allele present in a feral or wild cultivar exhibiting citrus-greening resistance and the root tissue is derived from a feral or wild cultivar exhibiting citrus-greening resistance. Numbered embodiment 61 comprises a citrus plant of numbered embodiments 1-60, wherein the plant yields commercially viable fruit at least 1 year after exposure to the citrus-greening disease. Numbered embodiment 62 comprises a citrus plant with improved viability following exposure to citrus greening disease compared to a plant sensitive to citrus greening disease. Numbered embodiment 63 comprises a citrus plant of numbered embodiments 1-61, wherein the plant is a graft. Numbered embodiment 64 comprises a citrus plant of numbered embodiments 1-62, wherein the plant is a hybrid. Numbered embodiment 65 comprises a citrus plant of numbered embodiments 1-64, wherein root tissue of the citrus plant comprises an allele absent from a citrus plant sensitive to the citrus greening disease. Numbered embodiment 66 comprises a citrus plant of numbered embodiments 1-65, wherein root tissue of the citrus plant comprises an allele present in a feral or wild cultivar exhibiting citrus-greening resistance and absent from a citrus plant sensitive to the citrus greening disease. Numbered embodiment 67 comprises a citrus plant of numbered embodiments 1-66, wherein root tissue of the citrus plant comprises an allele present in a feral or wild cultivar exhibiting citrus-greening resistance and root tissue of the citrus plant is derived from a feral or wild cultivar exhibiting citrus-greening resistance. Numbered embodiment 68 comprises a citrus plant of numbered embodiments 1-67, wherein the citrus plant demonstrates improved viability at least 1 year after exposure to the citrus-greening disease. Numbered embodiment 69 comprises a citrus plant that exhibits reduced symptoms of citrus greening disease following exposure to citrus greening disease compared to a citrus plant sensitive to citrus greening disease. Numbered embodiment 70 comprises a citrus plant of numbered embodiments 1-69, wherein the plant is a graft. Numbered embodiment 71 comprises a citrus plant of numbered embodiments 1-70, wherein the plant is a hybrid. Numbered embodiment 72 comprises a citrus plant of numbered embodiments 1-71, wherein root tissue of the citrus plant that exhibits reduced symptoms comprises an allele absent from the citrus plant sensitive to the citrus greening disease. Numbered embodiment 73 comprises a citrus plant of numbered embodiments 1-72, wherein root tissue the citrus plant that exhibits reduced symptoms comprises an allele present in a feral or wild cultivar exhibiting citrus-greening resistance and absent from the citrus plant sensitive to the citrus greening disease. Numbered embodiment 74 comprises a citrus plant of numbered embodiments 1-73, wherein root tissue of the citrus plant that exhibits reduced symptoms comprises an allele present in a feral or wild cultivar exhibiting citrus-greening resistance and the root tissue is derived from a feral or wild cultivar exhibiting citrus-greening resistance. Numbered embodiment 75 comprises a citrus plant of numbered embodiments 1-74, wherein the citrus plant exhibits reduced symptoms at least 1 year after exposure to the citrus-greening disease. Numbered embodiment 76 comprises a method of growing a plant using reduced pesticide comprising grafting a fruiting cultivar to a citrus-greening resistant rootstock and administering no more than 95% of a standard pesticide amount. Numbered embodiment 77 comprises a citrus plant that yields commercially viable fruit after exposure to water having elevated salt content. Numbered embodiment 78 comprises a citrus plant of numbered embodiments 1-77, wherein the plant is a graft. Numbered embodiment 79 comprises a citrus plant of numbered embodiments 1-78, wherein a rootstock of the plant is resistant to the water having the elevated salt content. Numbered embodiment 80 comprises a citrus plant of numbered embodiments 1-79, wherein the plant is a hybrid. Numbered embodiment 81 comprises a citrus plant of numbered embodiments 1-80, wherein the plant is transgenic. Numbered embodiment 82 comprises a citrus plant of numbered embodiments 1-81, wherein the plant is further resistant to citrus-greening. Numbered embodiment 83 comprises a citrus plant of numbered embodiments 1-82, wherein the plant maintains commercial viability after at least 1 week of exposure to the water having elevated salt content. Numbered embodiment 84 comprises a citrus plant of numbered embodiments 1-83, wherein the plant yields commercially viable fruit at least 1 year after exposure to the citrus-greening disease. Numbered embodiment 85 comprises a citrus plant of numbered embodiments 1-84, wherein the plant is grown using a watering regimen which provides a quantity of fresh water to the plant that is no more than 80% that provided to a corresponding commercial citrus plant. Numbered embodiment 86 comprises a citrus plant of numbered embodiments 1-85, wherein the quantity of fresh water is no more than 50% that provided to the corresponding commercial citrus plant. Numbered embodiment 87 comprises a citrus plant of numbered embodiments 1-86, wherein the quantity of fresh water is zero. Numbered embodiment 88 comprises a citrus plant of numbered embodiments 1-87, wherein the plant maintains commercial viability after 1 year of growth in the water with elevated salt content. Numbered embodiment 89 comprises a citrus plant of numbered embodiments 1-88, wherein the plant maintains commercial viability after 5 years of growth in the water with elevated salt content. Numbered embodiment 90 comprises a citrus plant of numbered embodiments 1-89, wherein the plant is grown at sea level. Numbered embodiment 91 comprises a citrus plant of numbered embodiments 1-90, wherein the salt content of the water with elevated salt content is 1,000 ppm to 35,000 ppm. Numbered embodiment 92 comprises a citrus plant of numbered embodiments 1-91, wherein the salt content of the water with elevated salt content is 5,000 ppm to 30,000 ppm. Numbered embodiment 93 comprises a citrus tree having at least one allele common to a feral or wild cultivar exhibiting citrus-greening resistance and absent from at least one commercial citrus tree line, and having at least one allele common to a commercial citrus tree line and absent from at least one wild cultivar exhibiting citrus-greening resistance. Numbered embodiment 94 comprises a citrus tree of numbered embodiments 1-93, wherein the plant has at least 50% of alleles in common with the at least one commercial citrus tree line. Numbered embodiment 95 comprises a citrus tree of numbered embodiments 1-94, wherein the plant has at least 75% of alleles in common with the at least one commercial citrus tree line. Numbered embodiment 96 comprises a citrus tree of numbered embodiments 1-95, wherein the plant has at least 87% of alleles in common with the at least one commercial citrus tree line. Numbered embodiment 97 comprises a citrus tree of numbered embodiments 1-96, wherein the plant has at least 93% of alleles in common with the at least one commercial citrus tree line. Numbered embodiment 98 comprises a graft tree having a root stock that is resistant to water having elevated levels of salt content. Numbered embodiment 99 comprises a graft tree of numbered embodiments 1-98, wherein the salt content is 1,000 ppm to 35,000 ppm. Numbered embodiment 100 comprises a graft tree of numbered embodiments 1-99, wherein the tree is further resistant to citrus-greening. Numbered embodiment 101 comprises a graft tree of numbered embodiments 1-100, wherein the tree yields commercially viable fruit at least 1 year after exposure to the citrus-greening disease. Numbered embodiment 102 comprises a graft tree of numbered embodiments 1-101, wherein the tree yields commercially viable fruit at least 1 year after exposure to the water having the elevated levels of salt. Numbered embodiment 103 comprises a graft tree of numbered embodiments 1-102, wherein the tree yields commercially viable fruit after exposure to a watering regimen comprising providing a quantity of fresh water to the plant that is no more than 80% that provided to a corresponding commercial citrus plant. Numbered embodiment 104 comprises a graft tree of numbered embodiments 1-103, wherein the quantity of fresh water is no more than 50% that provided to the corresponding commercial citrus plant. Numbered embodiment 105 comprises a graft tree of numbered embodiments 1-104, wherein the quantity of fresh water is zero. Numbered embodiment 106 comprises a graft tree of numbered embodiments 1-105, wherein the tree has at least 50% of alleles in common with at least one commercial citrus tree line. Numbered embodiment 107 comprises a graft tree of numbered embodiments 1-106, wherein the tree has at least 75% of alleles in common with at least one commercial citrus tree line. Numbered embodiment 108 comprises a graft tree of numbered embodiments 1-107, wherein the tree has at least 87% of alleles in common with at least one commercial citrus tree line. Numbered embodiment 109 comprises a graft tree of numbered embodiments 1-108, wherein the tree has at least 93% of alleles in common with at least one commercial citrus tree line. Numbered embodiment 110 comprises a seed of orange cultivar, wherein a representative sample of seed of said cultivar was deposited under ATCC Accession No. PTA-124301.

EXAMPLES

Example 1

The effects of flood and salinity stress on survival and performance of stress resistant orange trees were measured.

Orange seeds from fruits of trees derived from stress resistant rootstocks were grown. The orange seeds grew from seeds to the seedling stage and continued to grow to small trees. Four of the small trees were transferred to pots for continued growth. Some of the orange seedlings continued to grow from small trees to larger trees before being transferred to pots.

The four small orange trees were between 6 inches to 10 inches tall and the large orange tree was about 4 feet tall. The pots comprising the four small orange trees and the large orange tree were grown within 100 yards of a brackish river.

A category 5 hurricane hit the area, submerging the four small orange trees and the large orange tree. Following a week of the hurricane hitting the area, the trees remained submerged in flood water including water from the brackish river. The flood water covered the pots of the trees. Further, all of the four small orange trees and half the height of the large tree were still submerged under water. The trees remained submerged in brackish flood water for at least another week.

The four small orange trees and the large orange tree remained planted in their pots for several weeks. After such time, the water was drained from the pots. The four small orange trees and the large orange trees remained alive. Further, all the trees had their leaves intact and were flourishing.

This example shows that orange trees grown from stress resistant rootstocks are capable of surviving stress due to flooding and salinity.

Example 2

The effects of the bacterium *Candidatus* Liberibacter *asiaticus* on a first population of orange trees grown from cultivar scions grafted onto citrus-greening resistant rootstocks are compared to that of a second population of orange trees grown from cultivar scions grafted onto rootstocks which are not resistant to citrus greening.

The first population of orange trees is grown from Washington Navel cultivar scions grafted onto rootstocks resistant to citrus greening disease. The second population of orange trees is grown from Washington Navel cultivar scions grafted onto rootstocks not resistant to citrus greening disease. The two populations are planted and grown in soil within a closed field environment. The plants are irrigated and fertilized. After a year of growth, both populations are exposed to psyllids positive for the bacterium *Candidatus* Liberibacter *asiaticus*.

Following one year, parts of the plants from both populations, including roots and leaves, are observed for symptoms of citrus-greening disease. The number of non-green leaves is recorded and observed as a percentage of green leaves for each of the two populations. Roots and leaves of the two populations of plants are also analyzed biochemically. DNA is extracted from the roots and leaves of the two populations and analyzed by real time-PCR using primers to detect the *Candidatus* Liberibacter *asiaticus* gene.

The *Candidatus* Liberibacter *asiaticus* gene is undetectable in some plants grown from a Washington Navel cultivar scion grafted onto a citrus-greening resistant rootstock. These plants also do not display any symptoms of citrus-greening, such as yellow leaves. In some plants grown from a Washington Navel cultivar scion grafted onto a citrus-greening resistant rootstock, there is a detectable level of *Candidatus* Liberibacter *asiaticus* gene. These plants, however, are viable, can produce sweet fruit, and do not exhibit symptoms as severe as the plants grown from a Washington Navel cultivar scion grafted onto a rootstock that is not resistant citrus-greening.

The example illustrates that orange trees grown from a cultivar scion grafted onto a citrus-greening resistant rootstock are either resistant or less susceptible to the citrus-greening disease than orange trees that are grown from a cultivar scion grafted onto rootstock not resistant to citrus-greening.

Example 3

The effects of the bacterium *Candidatus* Liberibacter *asiaticus* on a first population of orange trees grown from cultivar scions grafted onto citrus-greening resistant rootstocks are compared to that of a second population of orange trees treated with pesticides which target the *Candidatus* Liberibacter *asiaticus* bacterium and/or vectors which carry the bacterium, and which are also grown from cultivar scions grafted onto rootstocks not resistant to citrus-greening.

The first population of orange trees is grown from Valencia cultivar scions grafted onto citrus-greening resistant rootstocks. The second population of orange trees is grown from Valencia cultivar scions grafted onto rootstocks not resistant to citrus-greening. A control population of orange trees is grown from Valencia seedlings (Control Population). The three populations are planted and grown in soil within a closed field environment. The plants are irrigated and fertilized. Pesticides which target the *Candidatus* Liberibacter *asiaticus* bacterium and/or vectors which carry the bacterium are administered once a week to the control population and second population. After a year of growth, all populations are exposed to psyllids positive for the bacterium *Candidatus* Liberibacter *asiaticus.*

Following one year, the roots and leaves of the orange trees from all three populations are observed for symptoms of citrus-greening disease. The number of non-green leaves is recorded and observed as a percentage of green leaves. Roots and leaves of the populations are also analyzed biochemically. DNA is extracted from the roots and leaves of all the populations and analyzed by real time-PCR using primers to detect the *Candidatus* Liberibacter *asiaticus* gene.

The *Candidatus* Liberibacter *asiaticus* gene is nearly undetectable in 60% of orange trees grown from cultivar scions grafted onto citrus-greening resistant rootstocks. There is a detectable level of a *Candidatus* Liberibacter *asiaticus* gene in 40% of these plants and they exhibit equal or less symptoms of citrus greening disease compared to plants grown from cultivars grafted to non-resistant rootstocks and treated with pesticides.

The orange trees from all three populations are then grown for an additional five years to assay for plant survival. 70% of the orange trees grown from cultivar scions grafted to citrus-greening resistant rootstocks, or the first population of orange trees, are viable and produce sweet fruits despite showing some symptoms of citrus-greening disease. In the control population, only 40% of the orange trees are viable and producing sweet fruits. Compared to orange trees grown from non-resistant rootstocks and treated with the pesticides, orange trees grown from cultivar scions grafted to citrus greening resistant rootstocks exhibit similar viability and productivity.

This example illustrates plants that are grown from cultivars grafted to citrus-greening resistant rootstocks exhibit either resistance or reduced symptoms compared to plants that are grown from cultivars grafted to non-resistant citrus greening rootstock and treated with pesticides

Example 4

Effects of the bacterium *Candidatus* Liberibacter *asiaticus* on a first population of orange trees treated with pesticides which target the bacterium *Candidatus* Liberibacter *asiaticus* and/or vectors of the bacterium, and which are grown from cultivar scions grafted onto citrus-greening resistant rootstocks, are compared to that of a second population of orange trees grown from cultivar scions grafted onto non-resistant citrus greening rootstocks and treated with the same pesticides.

The first population of orange trees is grown from Sunstar cultivar scions grafted onto citrus-greening resistant rootstocks. The second population of orange trees is grown from Sunstar cultivar scions grafted onto rootstocks not resistant to citrus-greening. A control population of orange trees is grown from Sunstar seedlings. The three populations are planted and grown in soil within a closed field environment. The plants are irrigated and fertilized. Pesticides which target the bacterium *Candidatus* Liberibacter *asiaticus* and/or vectors of the bacterium are administered once a week to all populations of orange trees. After a year of growth, all populations are exposed to psyllids positive for the bacterium *Candidatus* Liberibacter *asiaticus.*

Following one year of exposure to the psyllids positive for the bacterium *Candidatus* Liberibacter *asiaticus*, the roots and leaves of the orange trees are observed for symptoms of the citrus greening disease. The number of non-green leaves is recorded and observed as a percentage of green leaves. Roots and leaves of each of the populations are also analyzed biochemically. DNA is extracted from the roots and leaves of all the populations and analyzed by real time-PCR using primers to detect the *Candidatus* Liberibacter *asiaticus* gene.

The *Candidatus* Liberibacter *asiaticus* gene is nearly undetectable in about 80% of roots and leaves of the first population, orange trees grown from cultivars grafted onto citrus-greening resistant rootstocks and treated with the pesticides. There is a detectable level of a *Candidatus* Liberibacter *asiaticus* gene in the roots and leaves of about 20% of the first population. In the orange trees of the first population which exhibited detectable levels of the *Candidatus* Liberibacter *asiaticus* gene, the orange trees exhibited a similar or reduced number and/or degree of severity of symptoms of citrus-greening disease as compared to orange trees of the second population, the orange trees treated with the pesticides and grown from cultivar scions grafted to rootstocks not resistant to citrus-greening.

The orange trees of all three populations are then grown for an additional five years after exposure to the bacterium *Candidatus* Liberibacter *asiaticus*. Plant survival is assayed after the five year period. About 85% of the first population, or the orange trees grown from cultivar scions grafted onto citrus-greening resistant rootstocks and treated with the pesticides, are viable and produce sweet fruits despite showing some symptoms of citrus-greening disease. About 40% of plants in the control population are viable and producing sweet fruits. Orange trees grown from cultivar scions grafted to citrus-greening resistant rootstocks and treated with pesticides exhibit increased viability and productivity compared to orange trees grown from non-resistant rootstocks and treated with the pesticides.

This example illustrates plants that are grown from cultivar scions grafted to citrus-greening resistant rootstocks and treated with the pesticides exhibit greater viability and productivity than plants that are grown from cultivars grafted to non-resistant citrus greening rootstocks and treated with the pesticides.

Example 5

Effects of the brackish water upon a first population of orange trees which are grown from cultivar scions grafted onto brackish water resistant rootstocks, are compared to that of a second population of orange trees grown from cultivar scions grafted onto non-resistant citrus greening rootstocks.

The first population of orange trees is grown from Sunstar cultivar scions grafted onto brackish water resistant rootstocks. The second population of orange trees is grown from Sunstar cultivar scions grafted onto rootstocks not resistant to brackish water. A control population of orange trees is grown from Sunstar seedlings. The three populations are planted and grown in soil within a closed field environment at sea level. The plants are irrigated and fertilized. The plants are administered with a fresh water watering regimen that provides the plants with about 50% of fresh water that would typically be administered to commercial Sunstar trees.

Following one year of exposure to the brackish water, the roots and leaves of the orange trees are observed for symptoms of salinity stress. The number of non-green leaves is recorded and observed as a percentage of green leaves. Roots and leaves of each of the populations are also analyzed biochemically. Fruit yield is compared among the three categories.

About 80% of the first population, or the orange trees grown from cultivar scions grafted onto citrus-greening resistant rootstocks and treated with the pesticides, are viable and produce sweet fruits. About 20% of plants in each of the second population and control population are viable and producing sweet fruits.

This example illustrates plants that are grown from cultivar scions grafted to citrus-greening resistant rootstocks, grown in brackish water, exhibit greater viability and productivity than plants that are grown from cultivars grafted to non-resistant rootstocks.

While preferred embodiments of the present invention have been shown and described herein, it will be obvious to those skilled in the art that such embodiments are provided by way of example only. Numerous variations, changes, and substitutions will now occur to those skilled in the art without departing from the invention. It should be understood that various alternatives to the embodiments of the invention described herein may be employed in practicing the invention. It is intended that the following claims define the scope of the invention and that methods and structures within the scope of these claims and their equivalents be covered thereby.

What is claimed is:

1. A composite citrus tree comprising a fruiting cultivar scion grafted to a wild rootstock, wherein the wild rootstock is (a) obtained from a seed deposited under ATCC Accession No. PTA-124301 or (b) obtained from tissues of a plant grown from the seed deposited under ATCC Accession No. PTA-124301, wherein the composite citrus tree is resistant to citrus-greening and water having elevated levels of salt content of 50 ppm to 50,000 ppm, and wherein the composite citrus tree yields commercially viable fruit following exposure to a citrus greening disease and either coastal flood water or brackish groundwater.

2. The composite citrus tree of claim 1, wherein the fruiting cultivar scion is selected from cultivars of oranges, limes, lemons, pomelos, tangerines, and grapefruits.

3. The composite citrus tree of claim 1, wherein the fruiting cultivar scion is orange.

4. The composite citrus tree of claim 1, wherein the fruiting cultivar scion is selected from the group consisting of Washington Navel, Valencia, Trovita, Hamlin, Shamouti, Parson Brown, Pineapple, Queen, Sunstar, Gardner, Mid-Sweet, Blood Oranges, Lue Gim Gong, Rhode Island Valencia, and Homosassa.

5. The composite citrus tree of claim 1, wherein the composite citrus tree is exposed to coastal flood water.

6. The composite citrus tree of claim 5, wherein the composite citrus tree maintains commercial viability for at least 1 year following exposure to coastal flood water.

7. The composite citrus tree of claim 5, wherein the composite citrus tree maintains commercial viability after at least 1 day of exposure to coastal flood water.

8. The composite citrus tree of claim 7, wherein the composite citrus tree maintains commercial viability after at least 3 days of exposure to coastal flood water.

9. The composite citrus tree of claim 8, wherein the composite citrus tree maintains commercial viability after at least 1 week of exposure to coastal flood water.

10. The composite citrus tree of claim 1, wherein the composite citrus tree is exposed to brackish groundwater.

11. The composite citrus tree of claim 10, wherein the composite citrus tree is grown using a watering regimen which provides a quantity of fresh water to the plant that is no more than 80% of the water in the watering regimen.

12. The composite citrus tree of claim 11, wherein the composite citrus tree is grown using a watering regimen which provides a quantity of fresh water to the plant that is no more than 50% of the water in the watering regimen.

13. The composite citrus tree of claim 12, wherein the composite citrus tree is grown using a watering regimen which provides no fresh water to the plant.

14. The composite citrus tree of claim 1, wherein the composite citrus tree yields commercially viable fruit at least 1 year after exposure to the citrus-greening disease.

15. The composite citrus tree of claim 1, wherein the composite citrus tree yields commercially viable fruit after at least 1 day of exposure to the citrus-greening disease.

16. The composite citrus tree of claim 15, wherein the composite citrus tree yields commercially viable fruit after at least 1 week of exposure to the citrus-greening disease.

17. The composite citrus tree of claim 1, wherein the composite citrus tree is exposed to a combination of citrus greening disease and coastal flood water.

18. The composite citrus tree of claim 1, wherein the composite citrus tree is exposed to a combination of citrus greening disease and brackish groundwater.

\* \* \* \* \*